United States Patent
Huang et al.

(10) Patent No.: US 7,294,708 B2
(45) Date of Patent: Nov. 13, 2007

(54) TELOMERASE REVERSE TRANSCRIPTASE FRAGMENTS AND USES THEREOF

(75) Inventors: Jun Jian Huang, Beijing (CN); Cui-Fen Huang, Beijing (CN); Marie C. M. Lin, Hong Kong (CN); Hsiang-Fu Kung, Hong Kong (CN)

(73) Assignees: Beijing Institute of Biotechnology, Beijing (CN); The University of Hong Kong, Hong Kong (CN)

( * ) Notice: Subject to any disclaimer, the term of this patent is extended or adjusted under 35 U.S.C. 154(b) by 518 days.

(21) Appl. No.: 10/449,565

(22) Filed: May 30, 2003

(65) Prior Publication Data

US 2003/0225027 A1    Dec. 4, 2003

Related U.S. Application Data

(60) Provisional application No. 60/384,806, filed on May 31, 2002.

(51) Int. Cl.
*C07H 21/02* (2006.01)
*C12N 5/00* (2006.01)
*C12P 21/06* (2006.01)

(52) U.S. Cl. .................... 536/23.1; 435/325; 435/69.1

(58) Field of Classification Search .................... None
See application file for complete search history.

(56) References Cited

U.S. PATENT DOCUMENTS 6,166,178 A * 12/2000 Cech et al. .................. 530/324

FOREIGN PATENT DOCUMENTS

WO     WO98/21343    *   5/1998

OTHER PUBLICATIONS

Eck et al., (Gene-Based Therapy, In: The Pharmacological Basis of Therapeutics, Goodman and Gilman, Ed.s, 1996, pp. 77-101.*
Verma I and Somia N, Nature, 1997, vol. 389, pp. 239-242.*
Orkin et al., Report and Recommendation of the Panel to Assess the NIH Investment in Research on Gene Therapy, NIH, 1995.*

* cited by examiner

*Primary Examiner*—Shanon Foley
*Assistant Examiner*—Lei Yao
(74) *Attorney, Agent, or Firm*—Dickstein, Shapiro, LLP.

(57) ABSTRACT

The invention provides compositions comprising fragments of human telomerase reverse transcriptase (hTERT) which can lead to telomere dysfunction in a cell and reduction of growth and tumorigenicity in cancer cells. The invention also relates to uses of the fragments in the treatment of cancer and in drug discovery.

7 Claims, 7 Drawing Sheets

Figure 1:
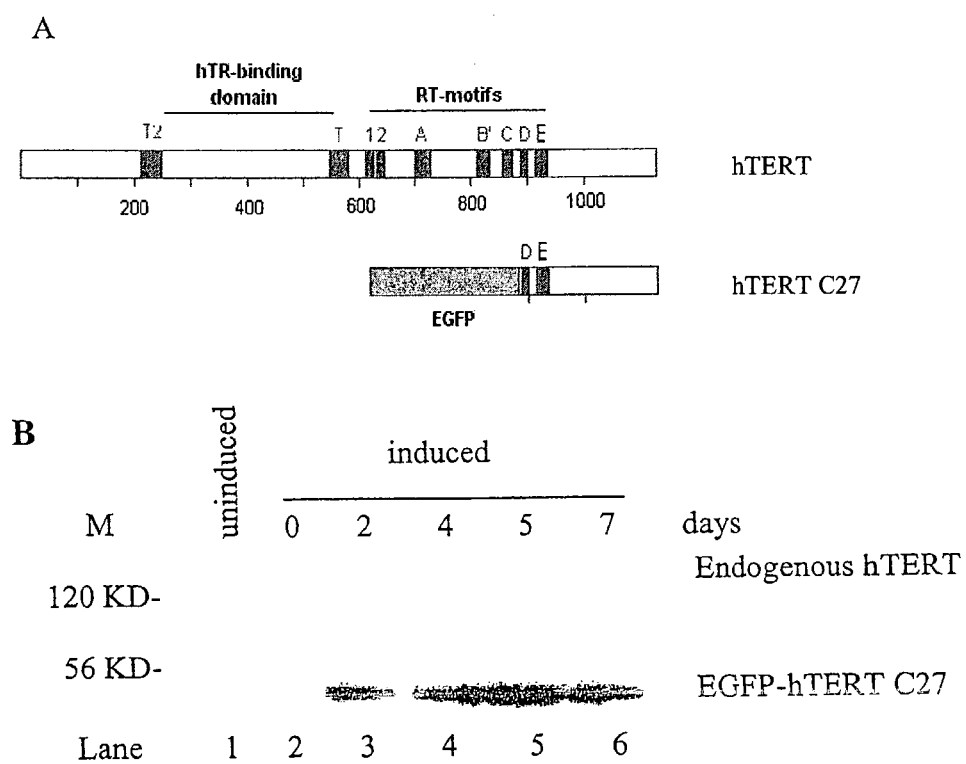

A
Uninduced (7 day)

B
Induced (4 day)

C
Induced (7 day)

D
(7 days after adding doxycyclin.)

A  (HeLa/ hTERT C27)    B  (HeLa/ EGFP)

1    2    3    4         1    2    3    4

TELOMERASE REVERSE TRANSCRIPTASE FRAGMENTS AND USES THEREOF

The present application claims the benefits of U.S. provisional application Ser. No. 60/384,806, filed May 31, 2002, which is incorporated herein by reference in its entirety.

1. INTRODUCTION

The present invention relates to fragments of telomerase reverse transcriptase and their methods of use in the treatment and prevention of cell proliferative diseases.

2. BACKGROUND OF THE INVENTION

Telomeres are special DNA-protein complexes at the end of chromosomes, whose major function is to protect chromosomes from degradation and end-to-end fusion, therefore, are essential for genome stability and cell survival (Blackburn, E. H., 2000, Nat. Struct. Biol., 7: 847-850; Counter et al., 1992, EMBO J., 11: 1921-1929). Acquiring the ability for telomere stabilization through telomerase reactivation has been proposed to be responsible for the immortal malignant phenotype of most cancer cells (Shay et al., 2001, Human Molecular Genetics, 10: 677-685).

Telomerase plays a pivotal role for the complete replication of the terminal telomeric DNA, which is a long stretch repetitive DNA sequence (TTAGGG in mammals). Telomerase activity is absent in most somatic cells in adult human tissues. Telomere lengths in normal cells shorten with each cell division, and progressive telomere shortening eventually results in cell senescence or crisis due to telomere dysfunction, characterized by mass genome instability (e.g. widespread chromosome end-to-end fusions), senescence-like growth arrest and apoptosis (Blackburn, E. H., 2000, Nature (Lond.), 408: 53-56; Blackburn, E. H., 2001, Cell, 106: 661-673). In more than 85% of all human cancer cells, telomerase is reactivated (Shay et al., 1997, J. Cancer, 33: 787-791), and the activation of telomerase activity has been shown to prevent telomere shortening, thereby immortalize cells (Bordnar et al., 1998, Science (Wash. D.C.), 297: 349-352; Vaziri et al., 1998, Curr. Biol., 8: 279-282). The expression of telomerase has also been demonstrated to be required both for the malignant transformation of normal human cells (Elenbaas et al., 2001, Genes Dev., 15: 50-65; Hahn et al., 1999, Nature (Lond.), 499: 464-468; Rich et al., 2001, Cancer Res., 61: 3556-3560) and the continued proliferation of cancer cells (Hahn et al., 1999, Nat. Med., 5: 1164-1170, Wu et al., 1999, Nat. Genet., 21: 220-224).

Telomerase is a ribonucleoprotein (RNA) complex with the telomerase RNA component (TR) and the catalytic protein subunit the telomerase reverse transcriptase (TERT) as its two core elements, which are conserved among all species (Harrington et al., 1997, Genes Dev., 11: 3109-3115; Nakamura et al., 1997, Science (Wash. DC), 277: 955-959; Weinrich et al., 1997, Nat. genet., 17: 498-505). The well-documented biological activity of TERT is to reverse transcribe the TR template into telomeric DNA sequence and elongate the telomere length. Therefore, TERT is a special reverse transcriptase. The TR gene is ubiquitously expressed in all human tissue (Avilion et al., 1996, Cancer Res., 56: 645-650, Feng et al., 1995, Science (Wash. DC), 269: 1236-1241), while the hTERT gene expression is restricted to only telomerase positive cells (e.g. germ lines, stem cells and most cancer cells) (Kilian et al, 1997, Hum. Mol. Genet., 6: 2011-2019), indicating that the expression of hTERT is a rate-limiting step for human cellular telomerase activity (Meyerson et al., 1997, Cell, 90: 785-795). Indeed, illegitimately induced expression of the TERT gene has been found to be the cause for telomerase reactivation in cancer cells. Consistently, many oncogenic proteins (such as c-Myc) act as the transcriptional activators for the TERT gene (Greenberg et al., 1999, Oncogene, 18: 1219-1226; Wu et al., 1999, Nat. Genet., 21: 220-224).

The functional domains of the hTERT protein include the hTR specific binding domain and the conserved reverse transcriptase motifs (RT-motifs), which are located at its N-terminal and the central regions of the protein, respectively (Bachand et al., 2001, Mol. Cell. Biol., 21: 1888-1897; Lai et al., 2001, Mol. Cell. Biol., 21: 990-1000; Nakamura et al., 1998, Cell, 92: 587-590). Both domains are required for the enzymatic activity of all TERT. Besides its hTR association and its reverse transcription activity, hTERT also needs to be localized to the nucleus to be functional. In yeast cells, this process is regulated by the specific interactions between the yeast telomerase-associated protein Est1 and the yeast telomeric single strand DNA specific binding protein Cdc13 (Evans et al., 1999, Science (Wash. DC), 286: 117-120, Lustig et al, 2001, Nat. Struct. Biol., 8: 297-299). The mechanism for recruiting hTERT to telomere end in human cells, however, has not been elucidated, neither is the human counter part for Est1 or Cdc13.

Because telomere stabilization through hTERT activation is critical for the long-term survival of cancer cells, specific interruption of this event may represent an excellent anti-cancer strategy. Up to date, most efforts were focused on inhibiting telomerase activity, thus leading to telomere shortening and ultimately inducing telomere dysfunction in cancer cells. The most commonly used strategies are either to specifically destroy the RNA template (TR) (Herbert et al., 1998, Proc. Natl. Acad. Sci. USA, 96:14276-14281; Kondo et al., 1998, Oncogene, 16: 3323-3330, Yokoyama et al., 1998, Cancer Res., 58: 5406-5410) or to inhibit the catalytic activity of TERT (Hahn et al., 1999, Nat. Med., 5: 1164-1170). These efforts have effectively led to telomerase suppression, progressive telomere shortening, telomere dysfunction, and ultimately marked inhibition of cell growth both in vitro and in vivo. Nevertheless, the inhibition of telomerase activity cause cancer cells to undergo a process to elicit the alternative lengthening of telomere (ALT) mechanism (Bryan et al., 1995, EMBO J. 14: 4240-4248), which is a telomerase-independent telomere maintaining pathway normally suppressed by telomerase activity (Ford et al., 2001, J Biol. Chem., 276: 32198-32203; Grobelny et al., 2001, Hum. Mol. Genet. 10: 1953-1961). This ALT mechanism uses the recombination-based pathway for telomere maintenance, and the activation of this pathway has previously been demonstrated in human cancer cells that are telomerase negative (Bryan et al., 1997, Nat. Med., 3: 1271-1274; Dunham et al., 2000, Nat. Genet., 26: 447-450).

Thus, there is a need for a better strategy that is more effective and less prone to the development of resistance. The present invention provides an approach that can produce a more favorable clinical outcome.

3. SUMMARY OF THE INVENTION

The invention relates to telomerase reverse transcriptase carboxyl terminal fragments (TERTC) polynucleotides, polypeptides, and analogs. The invention also encompasses uses of TERTC polynucleotides, polypeptides, and analogs for the prevention, treatment and management of cancer, particularly in cancer cells where telomerase is reactivated.

The present invention is based, at least in part, on the discovery that a hTERTC polypeptide causes a defect in telomere maintenance in hTERT positive HeLa cells.

TERTC proteins and variants thereof of the present invention are collectively referred to as "polypeptides" or "proteins" of the invention. Nucleic acid molecules encoding the polypeptides or proteins of the invention, or their complements thereof, are collectively referred to as "polynucleotides" or "nucleic acid sequences" of the invention.

The present invention provides isolated polynucleotides encoding a polypeptide of the invention. The invention further provides isolated polynucleotides, or variants thereof, which can be used, for example, for making the polypeptides of the invention. The present invention also encompasses DNA vectors that comprise polynucleotide of the invention. The invention also encompasses genetically engineered host cells or cancer cells that comprise any of the polynucleotides of the invention, operatively associated with a regulatory element that directs the expression of the polynucleotide in the host cell or cancer cell. Regulatory elements include, but are not limited to, inducible and non-inducible promoters, enhancers, operators and other elements that drive or regulate expression, which are known to the skilled artisan.

The present invention provides compositions comprising analogs of TERTC polypeptide. The present invention further provides methods for identifying such analogs which can be small molecules (i.e., less than 500 daltons) that acts similarly to a TERTC polypeptide when present in a cell. TERTC analogs may bind a binding partner of TERTC polypeptide to mediate its activity, wherein the binding partners include but are not limited to TRF2 and the ends of chromosomes.

The present invention also relates to a composition comprising a TERTC nucleic acid, TERTC polypeptide, a variant thereof, or TERTC analog, and optionally another therapeutic agent: In various embodiments, the invention provides for TERTC nucleic acid, TERTC polypeptide, a variant thereof, or TERTC analog, that is administered to a human, in combination with one or more cancer therapeutic agents, to prevent or treat cancer. Such cancer therapeutics include one or more molecules, compounds or treatments that have anti-cancer activity. Examples of contemplated therapeutics include biologicals, chemicals, and therapeutic treatments (e.g., irradiation treatment). Pharmaceutical compositions comprising one or more of the foregoing and a pharamceutically acceptable carrier are also included.

The present invention also relates to a method for preventing or treating a cell proliferative disorder including but not limited to cancer, comprising administering to a patient in need thereof an effective amount of a TERTC nucleic acid, TERTC polypeptide or a variant thereof, or TERTC analog. The present invention also relates to a method for increasing a patient's sensitivity to a therapeutic agent, comprising administering to a patient in need thereof an effective amount of a TERTC nucleic acid, TERTC polypeptide or a variant thereof, or a TERTC analog. Accordingly, a TERTC nucleic acid, TERTC polypeptide, a variant thereof, or TERTC analog is administered, to a patient in need of such treatment, to prevent or treat cancer, such as but not limited to when telomerase mRNA or protein is expressed at above-normal levels.

The present invention further provides methods for increasing the sensitivity of a cancer cell to oxidative stress comprising contacting the cancer cell with an effective amount of a TERTC nucleic acid, TERTC polypeptide or a variant thereof, or TERTC analog. The effects of oxidative stress on cancer cells include changes in morphology and induction of senescence. The methods can also be used to reduce the resistance of cancer cells to treatment with an anticancer drug that functions by generating oxidative stress in the cancer cells. Thus, the TERTC nucleic acid, TERTC polypeptide, a variant thereof, and TERTC analog can be used to enhance and/or prolong the therapeutic benifits of an anticancer drug.

The invention also provides for drug delivery means and therapeutic regimens for the pharmaceutical compositions of the invention. In one embodiment, the pharmaceutical compositions of the invention are delivered by gene therapy.

3.1 Definitions

As used herein the term "hTERT" refers to the human telomerase reverse transcriptase. The phrase "TERTC nucleic acid" or "TERTC polynucleotide" refers to a polynucleotide derived from the 3' end of a telomerase reverse transcriptase gene, including the complementary sequences thereof, and variants thereof.

The phrase "TERTC polypeptide" refers to a protein, polypeptide, peptide, and variants thereof, derived from the carboxyl terminal of a telomerase reverse transcriptase. The prefix "h" may be added to indicate the human origin of the nucleic acid or polypeptide.

As used herein, the term "variant" or "variants" refers to, where appropriate, variations of the nucleic acid or amino acid sequence of TERTC molecules such as, but not limited to, polypeptides encoded by mRNA splice variants, homologs, analogs, derivatives, fragments, hybrids, mimetics, congeners, and nucleotide and amino acid substitutions, additions, deletions, or other chemical modifications.

As used herein, the phrase "TERTC gene expression" refers to transcription of a TERTC gene which produces TERTC pre-mRNA, TERTC mRNA, and/or translation of TERTC mRNA to produce TERTC polypeptide.

As used herein, the phrase "therapeutics" or "therapeutic agents" refer to any molecules or compounds that assist in the treatment of a disease. As such, a cancer therapeutic is a molecule or compound that aids in the treatment of tumors or cancer. A treatment protocol includes, but is not limited to, administration of therapeutic agents, radiation therapy, dietary therapy, physical therapy, and psychological therapy. Cancer therapeutics also encompass a molecule or compound that aids in the prevention of tumors or cancer, prevents the recurrence of tumors or cancer, or prevents the spread or metastasis of tumors or cancer.

4. BRIEF DESCRIPTION OF THE DRAWINGS

FIGS. 1A-1B. Design and the expression of a truncated C-terminus hTERT 27 kDa polypeptide. (A) The structure of the full-length hTERT and the truncated mutant hTERT C27. To facilitate the detection of its expression and cellular localization, the truncated hTERT C27 is linked to a N-terminal EGFP tag. (B) Western blotting analysis of the regulated expression of the truncated hTERT C27 polypeptides. Whole-cell extracts were prepared from a clone (C8) of HeLa Tet-off cells stably expressing the pTetEGFP-hTERT C27 plasmid. The cells were maintained in medium supplemented with doxycycline. At the beginning of the experiments, doxycycline were withdrawn from the medium to induce the expression of EGFP hTERT C27 for the indicated amount of time. In each lane 40 µg of protein was loaded. Western analysis was performed with specific antibody against the hTERT C-terminal polypeptide (Santa Cruz, sc-7212). The endogenous hTERT (127 KD) were detected using longer exposure time. The data shown is obtained from a representative experiment using a single clone of hTERT C27 expressing cells.

FIGS. 2A-2E. Effect of hTERT C27 over-expression on growth inhibition and apoptosis. (A) Growth curve showing the effect of either the vector pRevTRE (left panel) or EGFP hTERT C27 (right panel) expression on the growth of HeLa cells. Cell numbers were counted based on the trypan blue assay. (B-D) Flow-cytometry analysis of cells double labeled with annexin V and propidium iodide (PI). Cells were harvested at indicated time points post-induction. (E) Summary of the data from the flow-cytometry analysis.

FIGS. 3A-3D. Induction of senescence by hTERT C27 over-expression. Morphological of the HeLa Tet-off clone C8. (A) non-induced; (B) induced to express the hTERT C27 for 4 days; (C) induced to express hTERT C27 for 7 days; (D) induce to express hTERT C27 for 6 days followed by suppression of hTERT C27 expression for 7 days. Cells were stained for β-galactosidase activity at pH 6.0 and photographed using a phase-contrast microscope.

FIGS. 4A-4H. Subcellular localization of hTERT C27 and induction of chromosome end to end fusions by the hTERT C27 polypeptide. HeLa Tet-off clone C8 was induced to express hTERT C27 for 4 days. The subcellular localization of the over-expressed hTERT C27 was analyzed by fluorescence microscopy using the EGFP tag as a tracer. Cells were then fixed by methanol and stained with PI for analysis of aberrant chromosome events. (A) The expressed hTERT C27 localized in nucleous and showed the punctate pattern (green) in a living HeLa cells. (B-G) The chromosomal DNA (stained with PI and shown as red), and the overlapped images of the EGFP signal for hTERT C27 (shown as yellow). Localization of the ectopic expressed hTERT C27 in (B) an interphase nucleus; and (C) a mitotic chromosome. Four anaphase cells displayed hTERT C27 induced (D) anaphase bridges; and (E-G) lagging chromosomes. (H) HeLa cells transiently transfected with the C-termius modified EGFP-hTERT C27-HA plasmid and showed diffuse nuclear localization and no punctate chromosome pattern.

Figure 5:
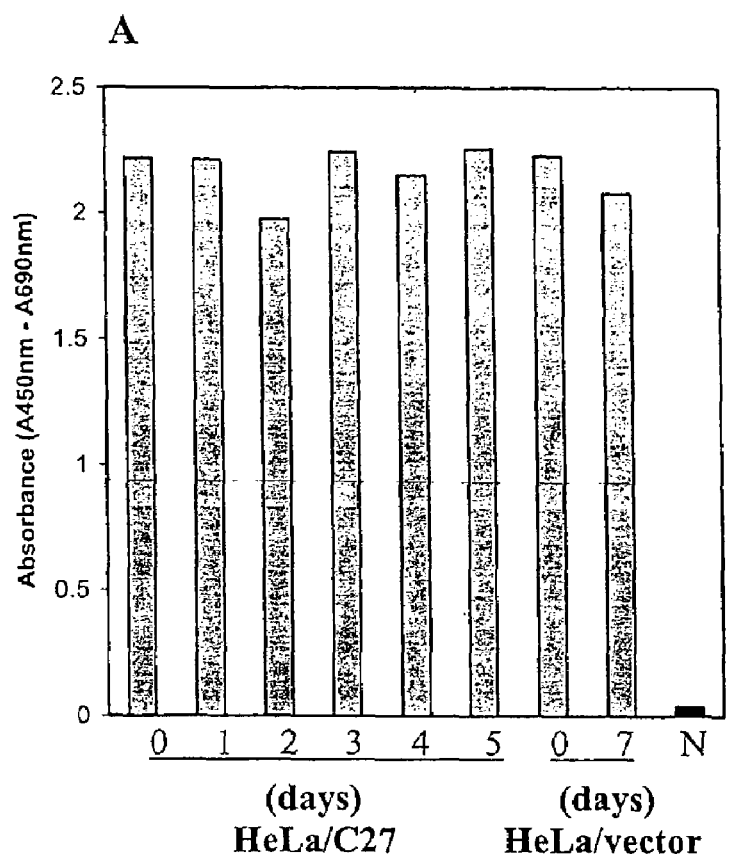
Figure 5:
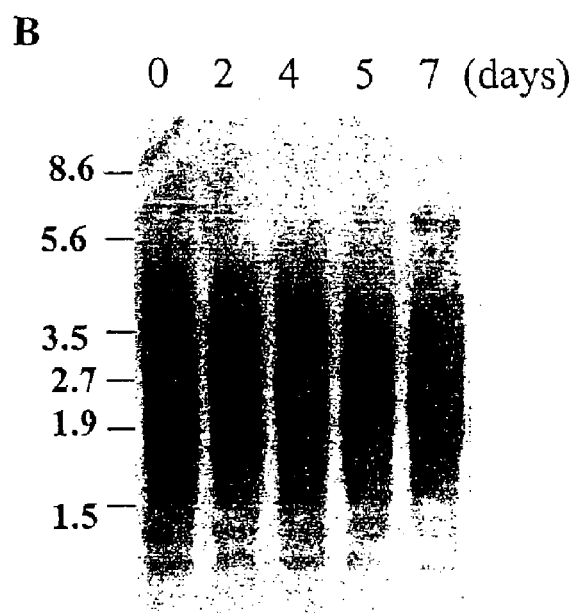

FIGS. 5A-5B. Effects of ectopic expression of hTERT C27 on telomerase activity and telomere lengths. (A) Whole-cell extracts were prepared from HeLa Tet-off cells at indicated time points after induction to express hTERT C27. Telomerase activity was detected by the TRAP-ELISA assay with a telomerase PCR ELISA Kit (Roche). Three μg of protein was used for each telomerase detection reaction. The data represent the average values of three independent experiments for each sample. (B) Genomic DNA were prepared from cells at indicated time points after induction for hTERT C27 expression. For each sample, 2 μg of genomic DNA were digested with the Rsa I and Hinf I. Telomere lengths were detected by the terminal restriction fragment assay with a Telo TTAGGG telomere length assay kit (Roche).

FIGS. 6A-6B. hTERT C27 reduced HeLa cell tumorigenicity in the xenografted nude mice model. Photographs of nude mice (n=4 per group) injected s.c. with either (A) the hTERT C27 expressing HeLa cells ($2\times10^6$ cells/mouse); or (B) the control EGFP expressing HeLa cells ($2\times10^6$ cells/mouse). The growth rates of the solid tumors were monitored weekly for 4 weeks. At the end of the experiments, mice were sacrificed and photographs were taken to view the solid tumor formations. The experiments were repeated twice and the representative results shown.

Figure 7:
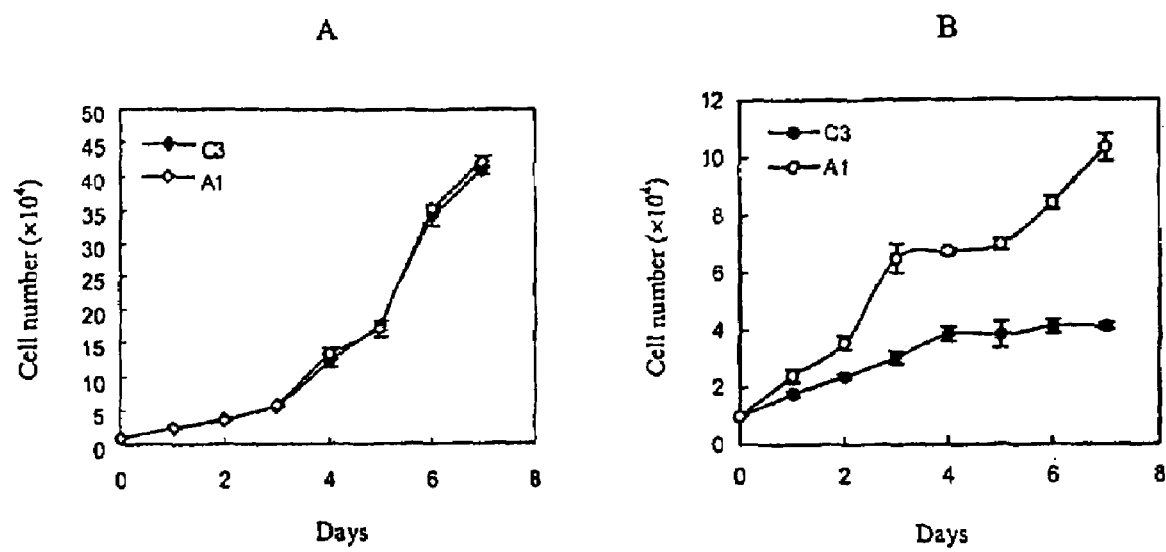

FIG. 7. Low level expression of hTERTC27 in HeLa cells did not change the rate of cell proliferation but sensitized cells to $H_2O_2$-induced oxidative stress. Cell numbers were determined by measuring the number of viable cells per well using the trypan blue method. (A) The C3 clone (stably expressing EGFP-hTERTC27), A1 clone (stabling expressing EGFP), and the parental HeLa cell line were seeded ($2\times10^4$ cells per well) and maintained in 24-well plates. (B) A1 and C3 cell lines were seeded ($1\times10^4$ cell per well) to 24-well plates after a 2 h bolus dose of 100 μM $H_2O_2$ treatment.

5. DETAILED DESCRIPTION OF THE INVENTION

The present invention provides telomerase reverse transcriptase carboxyl terminal fragments (TERTC) and variants thereof. The invention also relates to polynucleotides that encodes the TERTC polypeptides and variants thereof of the invention. The invention also relates to analogs of TERTC polypeptide, or molecular complexes comprising a TERTC polypeptide. The invention also relates to methods of identifying binding partners of a TERTC polypeptide. Further, the invention relates to prevention or treatment of cancer, particularly cancers where telomerase is reactivated, comprising administering a TERTC polynucleotide, TERTC polypeptide, TERTC analog, with or without additional therapeutic agents.

Telomerase is a ribonucleoprotein complex (RNP) comprising an RNA component and a catalytic protein component. Human telomerase reverse transcriptase (hTERT) is the catalytic component of human telomerase, which is a 127 KDa protein consisting of 1132 amino acid residues. Human telomerase reverse transcriptase has been cloned, and protein, cDNA and genomic sequences determined. See, e.g., Nakamura et al., 1997, Science 277:955; GenBank Accession No. AF015950 and AAC51672. The catalytic subunit protein of human telomerase has also been referred to as "hEST2" (Meyerson et al., 1997, Cell 90:785), "hTCS1" (Kilian et al., 1997, Hum. Mol. Genet. 6:2011), "TP2" (Harrington et al., 1997, Genes Dev. 11:3109), and "hTRT" (e.g., U.S. Pat. No. 6,337,200). It contains a specific binding domain for telomerase RNA (hTR)(FIG. 1A shaded boxes: T, T2 are the two conserved motifs) which is located in its N-terminus (Bachand et al., 2001, Mol. Cell Biol. 21:1888-1897), and a reverse transcriptase (RT)-domain (FIG. 1A shaded boxes: 1, 2, A, B', C, D, E represent seven conserve short motifs), which occupy its central region. These two functional domains are both required for the catalytic reverse transcriptase activity of hTERT. The hTERT C-terminal region consists of about 200 amino acid residues and contains the nuclear export signal (residues 970-981) and the 14-3-3 binding amphipathic helix (residues 1030-1047) responsible for the nuclear translocalization of the hTERT protein (Seimiya et al., 2000, EMBO J. 19:2652-61).

The present invention is based, at least in part, on the discovery that a TERTC polypeptide causes a defect in telomere maintenance in TERT positive HeLa cells, which resulted in senescence-like growth arrest and apoptosis. The inventors constructed plasmids expressing the C-terminal 27 kDa polypeptide of hTERT (C27). In this hTERT C27 construct, the N-terminal 881 amino acids of the hTERT, which includes the hTR-binding domains and most of the RT-domains, is deleted. The overexpressed hTERT C27 exerts its effects through induction of telomere dysfunction, exemplified by significantly increased anaphase chromosome end-to-end fusion events in transfected cells, which preceded cellular senescence and apoptosis. The inventors further showed that HeLa cells expressing hTERTC27 became sensitive to a mild sub-lethal dose of hydrogen peroxide and progressed to a senescence-like growth arrest. This sensitivity is associated with an up-regulation of the cyclin/cdk inhibitor p21$^{waf1}$ without any change in p53 level. Significantly, it had no effect on the cellular telomerase enzymatic activity or telomere length. The effect of hTERT C27 on HeLa cell tumorigenicity was further investigated in vivo in nude mice xenograft.

Without being bound by any theory, the inventors believe that, TERT, through its C-terminus polypeptide, confers a role in the protection of functional telomere structure, specifically on the content of shorter telomeric DNA lengths seen in cancer cells. The hTERT C-terminus contains one or more functional motifs, which play important biological roles in the maintenance of the integrity of telomere and telomere structure, as well as cell immortalization. The inventors also believe that the binding of hTERT C-terminal polypeptide on telomeres distorts the capped telomere structures. This can in turn affect the affinity or transport of DNA damage-responding proteins that are naturally associated with the telomeres resulting in the enhanced sensitivity of TERT-positive cancerous cells to oxidative stress.

The TERTC polypeptides, variants, fuison proteins and analogs, are described in greater detail in Section 5.1 and 5.5. The present invention further provides polynucleotides encoding TERTC polypeptides and variants thereof, fusion proteins, analogs, which are described in details in Section 5.2 hereinbelow. Production of the foregoing TERTC polypeptides, proteins and analogs by recombinant DNA methods, are also provided and is described in Section 5.3. Antibodies against TERTC polypeptides and variants thereof are described in Section 5.4.

The present invention also relates to therapeutic methods and compositions based on TERTC polypeptides and variants thereof, fusion proteins, analogs, and TERTC polynucleotides. The invention provides for the use of such compositions to inhibit the growth and proliferation of cancer cells. The invention also provides for the use of such compositions to sensitize cancer cells to anticancer drugs, such as chemotherapeutic agents, to prevent the development of cellular resistance to such drugs, or to reduce cellular resistance to anticancer drugs. The benefits include the possibility of using a lower dose of the anticancer drug or a prolonged period of usefulness of a drug against a cancer. Methods of uses are described in details in Section 5.6.

In the Examples, HeLa cells overexpressing C27 are shown to have significantly lower growth rate and reduced tumorigenicity in nude mice xenograft. Results from the examples demonstrated that the ectopic overexpressed C-terminus of TERT has a profound effect in the maintenance of telomere integrity and the induction of chromosome end-to-end fusions as well as cell senescence and apoptosis. The data also indicated that low level of expression of C27 rendered HeLa cells sensitive to hydrogen peroxide-induced cellular senescence. The results provide a new strategy for cancer therapy by the induction of telomere dysfunction in cancer cells without affecting the telomerase enzymatic activity.

For clarity of disclosure, and not by way of limitation, the detailed description of the invention is divided into the subsections which follow.

5.1 TERTC Polypeptides.

In one embodiment, the present invention provides TERTC polypeptides and variants thereof, and TERTC analogs. The TERTC polypeptides of the present invention are characterized by one or more deletions relative to a naturally occurring TERT polypeptide of human and non-human species. The deletions are in the amino terminal and extend to the RT-motifs of TERT. In a specific embodiment, the TERTC polypeptide is a truncated TERT in which the region from the amino terminal up to the conserved motifs in the RT domain is deleted. One or more of the conserved motifs may be deleted, and in a specific embodiment, the deletion extends from amino acid residue 1 to about 881 of hTERT. In a preferred embodiment, a TERTC polypeptide consists essentially of the amino acid residues 882 to 1132 of hTERT, which is a polypeptide of about 251 amino acids and of about 27 kDa. A preferred example of a TERTC polypeptide is the C27 polypeptide (hTERT C27 or hTERTC27) (SEQ ID NO:2) which consists of the amino acid residues of 882 to 1132 of hTERT.

In various embodiments, a TERTC polypeptide comprises substantially the amino acid sequence of the carboxyl terminal of a TERT, has a size range of from 25 to 30 kDa and display at least one of the functional characteristics of its prototype as demonstrated by the C27 polypeptide. Examples include polypeptides which comprise a subsequence of the amino acid sequence of C27 polypeptide, about 220 to 251 amino acids and which display at least one of the functional characteristics of the C27 polypeptide.

In specific embodiments, the invention excludes certain deletion mutants of human TERT which are described in Seimiya et al. 2000, EMBO J, 19:2652-2661. In particular, the invention encompasses isolated polypeptides derived from the carboxyl terminal of human TERT with the proviso that the isolated polypeptides do not consist of the following three amino acid sequences from the hTERT coding sequences: residues 831 to 1132; residues 831 to 1004; and residues 1004 to 1132.

Functionally, a TERTC polypeptide lacks telomerase catalytic activity, i.e., less than 1% of that of the naturally occurring enzyme. Furthermore, a TERTC polypeptide of the invention, when expressed in a cell, lacks inhibitory effect on the telomerase activity in a cell, i.e., it does not act as a "dominant negative mutant". The telomerase activity in the cell is from a full length wild type functional TERT, preferably of the same species.

Importantly, TERTC polypeptides display unexpected anti-proliferative properties when expressed in a cancer cell. Accordingly, in one aspect, a TERTC polypeptide is characterized by its ability to cause telomere dysfunction in cancer cells, to increase in cancer cells the frequency of aberrant chromosomes and/or aberrant chromosomal structures, such as anaphase bridges, which can be caused by chromosome end-to-end fusion. In another aspect, a TERTC polypeptide, when expressed in a cell, induces a phenotype that is characteristic of a disruption of the binding of telomere binding protein TRF2 to telomere, see van Steensel et al., 1998, Cell, 92:401-413.

In another aspect, a TERTC polypeptide is characterized by its ability to cause senescence-like growth arrest in cancer cells. By "senescence-like growth arrest" is meant the loss of ability of a cell to replicate in the presence of normally appropriate replicative signals, and may be associated with the expression of degradative enzymes, such as collagenase. As most normal somatic cells derived from adults are limited in the number of times they can divide, the number of replicative events that a cell or cell line can undergo before replicative arrest is known as the Hayflick limit. For example, HeLa cells expressing C27 display a phenotype that resembles cells that approach the Hayflick limit.

In yet another aspect, a TERTC polypeptide is characterized by its ability to cause apoptosis in cancer cells. In yet another aspect, a TERTC polypeptide is capable of reducing the tumorigenicity of a cancer cell in vivo. As demonstrated in the Examples hereinbelow, the hTERT C27 polypeptide displays each of these functional characteristics.

The TERCT polypeptides of the invention can be isolated, using standard protein purification techniques, from cells expressing a TERTC polypeptide. In a preferred embodiment, polypeptides of the invention are produced from expression vectors in a human cell by recombinant DNA techniques. In another preferred embodiment, a polypeptide of the invention is synthesized chemically using standard peptide synthesis techniques. In yet another embodiment, a TERTC polypeptide can be prepared by partial protease digestion of the full length TERT polypeptide.

An isolated or purified protein or biologically active portion thereof is substantially free of cellular material or other contaminating proteins from the cell or tissue source from which the protein is derived, or substantially free of chemical precursors or other chemicals when chemically synthesized. The language "substantially free" indicates protein preparations in which the protein is separated from cellular components of the cells from which it is isolated or recombinantly produced. Thus, protein that is substantially free of cellular material includes protein preparations having less than 20%, 10%, or 5% (by dry weight) of a contaminating protein. Similarly, when an isolated TERTC polypeptide of the invention is recombinantly produced, it is substantially free of culture medium. When the TERTC polypeptide is produced by chemical synthesis, it is preferably substantially free of chemical precursors or other chemicals.

Variants of a TERTC polypeptide of the invention include polypeptides comprising amino acid sequences similar to or derived from the amino acid sequence of the TERTC polypeptide, such that the variants sequences comprise conservative substitutions or truncations. Also encompassed are variants that comprise subsequences—amino acid sequences comprising fewer amino acids than those shown in SEQ ID NO:2, but which maintain a high degree of homology to the remaining amino acid sequence. Typically, variants comprise a domain or motif with at least one activity of a TERTC polypeptide. Domains or motifs include, but are not limited to, a biologically active portion of a TERTC polypeptide of the invention which is, for example, at least 10, 25, 50, 100, 150, 200, or 250 amino acids in length. TERTC polypeptides of the invention can comprise, for example, phosphorylation sites, glycosylation signals, subcellular localization signals such as the nuclear export signal (residues 970-981 in hTERTC) and the 14-3-3 binding amphipathic helix (residues 1030-1047).

In various embodiments, as telomerase is believed to be present in most eukaryotes, fragments of TERT of non-human species can also be used as TERTC polypeptide provided that the fragment displays at least one of the characteristics of TERTC polypeptide.

A preferred TERTC polypeptide, namely hTERTC C27, consists of the amino acid sequence of SEQ ID NO:2. Other useful hTERTC polypeptides are substantially identical (e.g., at least 65%, preferably 75%, 85%, 90%, 95%, or 99%) to SEQ ID NO:2. In certain embodiments, the invention provides fragments of the amino acid sequence wherein the percent identity is determined over amino acid sequences of identical size to the fragment. In other embodiments, the invention provides a polypeptide comprising an amino acid sequence that has at least 90% identity to the fragments of domains identified in the TERTC polypeptide, wherein the percent identity is determined over an amino acid sequence of identical size to said fragment.

The determination of percent identity between two sequences can be accomplished using a mathematical algorithm. A preferred, non-limiting example of a mathematical algorithm utilized for the comparison of two sequences is the algorithm of Karlin and Altschul (1990, Proc Natl Acad Sci. 87:2264-2268), modified as in Karlin and Altschul (1993, Proc Natl Acad Sci. 90:5873-5877). Such an algorithm is incorporated into the NBLAST and XBLAST programs of Altschul et al. (1990, J. Mol. Biol. 215:403-410). BLAST nucleotide searches can be performed with the NBLAST program, score=100, wordlength=12 to obtain nucleotide sequences homologous to a polynucleotides of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997, Nucleic Acids Res. 25:3389-3402). Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the web site of National Center for Biotechnology Information (NCBI).

Another preferred, non-limiting example of a mathematical algorithm utilized for the comparison of sequences is the algorithm of Myers and Miller, (1988, CABIOS 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994, Comput. Appl. Biosci. 10:3-5); and FASTA described in Pearson and Lipman (1988, 85:2444-2448). Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see the "Biological software" at the Institute Pasteur's web site.

The percent identity between two sequences can be determined using techniques similar to those described above, with or without allowing gaps. In calculating percent identity, only exact matches are counted. However, conservative substitutions should be considered in evaluating sequences that have a low percent identity with the TERTC sequences disclosed herein.

Variants of the TERTC polypeptides of the invention have an altered amino acid sequence which can be generated by mutagenesis, e.g., discrete point mutation or truncation. A variant can retain substantially the same, or a subset, of the biological activities of the TERTC polypeptide. Thus, specific biological effects can be elicited by treatment with a variant of a TERTC polypeptide.

Variants of a TERTC polypeptide of the invention the functions of which can be identified by screening combinatorial libraries of mutants of the TERTC fragment of the invention for one or more biological activities. In one embodiment, a library of variants is generated by combinatorial mutagenesis at the nucleic acid level. Such a library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (See, e.g., Narang, 1983, Tetrahedron 39:3; Itakura et al., 1984, Annu Rev Biochem. 53:323; Itakura et al., 1984, Science 198:1056; Ike et al., 1983, Nucleic Acid Res. 11:477).

Moreover, variants of a TERTC polypeptide of the invention can be produced by DNA shuffling and directed evolution techniques. For example, recursive ensemble mutagenesis, a technique which enhances the frequency of functional mutants in the libraries, can be used in combination with the functional assays to identify variants of a TERTC polypeptide of the invention (See, e.g., Arkin and Yourvan, 1992, Proc Natl Acad Sci. 89:7811-7815; Delgrave et al., 1993, Protein Engineering 6:327-331).

The TERTC polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). The TERTC polypeptides of the invention can, for example, include modifications that can increase such attributes as stability, half-life, ability to enter nucluss and aid in administration, e.g., in vivo administration of the TERTC polypeptides of the invention.

The invention also provides chimeric or fusion proteins. As used herein, a "chimeric protein" or "fusion protein" comprises all or part (preferably biologically active) of a TERTC polypeptide of the invention fused in-frame to a second polypeptide. In one embodiment, the second polypeptide is a heterologous polypeptide. In another embodiment, the second polypeptide is different from, but derived from the same, polypeptide to which it is attached. The second polypeptide can be fused to the N-terminus or C-terminus of the TERTC polypeptide of the invention. Preferably, the second polypeptide is fused to the N-terminus of TERTC polypeptide.

As described in Section 6, one such fusion is EGFP-hTERTC27 which consists of the enhanced green fluorescent protein (EGFP) fused to the amino terminus of the C27. This fusion protein facilitates observation of the synthesis and transport of C27 inside a cell. Another useful fusion protein is a GST fusion protein in which the polypeptide of the invention is fused to the C-terminus of GST sequences. Such GST-based constructs can facilitate the purification of a recombinant polypeptide of the invention.

In another embodiment, the fusion protein comprises a heterologous signal sequence at its N-terminus. As used herein, a signal sequence (or signal peptide or secretion signal), refers to a peptide of at least about 15 or 20 amino acid residues in length which occurs at the N-terminus of secretory and membrane-bound proteins and which comprises at least about 70% hydrophobic amino acid residues such as alanine, leucine, isoleucine, phenylalanine, proline, tyrosine, tryptophan, or valine. A signal sequence serves to direct a protein comprising such a sequence to a lipid bilayer or the exterior of a cell. A signal sequence is usually cleaved during processing of the mature protein. The TERTC polypeptide can then be readily purified from the extracellular medium by art recognized methods. For example, useful prokaryotic heterologous signal sequences include the phoA secretory signal (Sambrook et al., supra) and the protein A secretory signal (Pharmacia Biotech; Piscataway, N.J.).

Chimeric and fusion proteins of the invention can be produced by standard recombinant DNA techniques. In one embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a TERTC polypeptide of the invention can be cloned into such an expression vector such that the fusion moiety is linked in-frame to the polypeptide of the invention.

The polypeptides, variants, and analogs of the invention also encompasses complexes comprising TERTC polypeptide and at least one binding partner selected from the group consisting of the telomerase RNA, and chromosomal DNA.

5.2 TERTC Polynucleotides.

In another embodiment, the present invention provides TERTC polynucleotides that encode TERTC polypeptide and variants thereof as described in Section 5.1. The TERTC polynucleotides of the invention can be used to express proteins, for example, via a recombinant expression vector in a cancer cell in gene therapy applications, or in a host cell to make a TERTC polypeptide.

A polynucleotide is intended to include DNA molecules (e.g., cDNA, genomic DNA), RNA molecules (e.g., hnRNA, pre-mRNA, mRNA), and DNA or RNA analogs generated using nucleotide analogs. The polynucleotide can be single-stranded or double-stranded. An "isolated" polynucleotide, such as a cDNA molecule, can be substantially free of other cellular material, or culture medium when produced by recombinant techniques, or substantially free of chemical precursors or other chemicals when chemically synthesized. As used herein, an isolated polynucleotide does not include an isolated chromosome, and does not include the poly(A) tail of an mRNA, if present. However, a TERTC polynucleotide can comprise cDNA, genomic DNA, introns, exons, promoter regions, 5' regulatory regions of a TERT gene, 3' regulatory regions of a TERT gene, RNA, hnRNA, mRNA, and regulatory regions within RNAs.

In a preferred embodiment, the TERTC polynucleotides are of human origin. The invention provides a nucleotide sequence which encodes hTERT C27 and which is set forth in SEQ ID NO: 1. Human telomerase reverse transcriptase has been cloned, and protein, cDNA and genomic sequences determined. See, e.g., Nakamura et al., 1997, Science 277: 955 and GenBank Accession No. AF015950. The catalytic subunit protein of human telomerase has also been referred to as "hEST2" (Meyerson et al., 1997, Cell 90:785), "hTCS1" (Kilian et al., 1997, Hum. Mol. Genet. 6:2011), "TP2" (Harrington et al., 1997, Genes Dev. 11:3109), and "hTRT" (e.g., U.S. Pat. No. 6,337,200).

A polynucleotide that encodes a variant TERTC polypeptide can be created by introducing one or more nucleotide substitutions, additions or deletions into the nucleotide sequence of SEQ ID NO: 1, or starting with the full length nucleotide sequence of hTERT (GenBank Accession No.

AF015950) using any method known in the art. In one embodiment, such methods introduce one or more amino acid substitutions, additions or deletions are introduced into the encoded polypeptide.

For example, mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Using all or a portion of the nucleic acid sequence of SEQ ID NO:1 or GenBank Accession No. AF015950 to make a hybridization probe, polynucleotides of the invention can be isolated using standard hybridization and cloning techniques (See, e.g., Sambrook et al., Molecular Cloning: A Laboratory Manual, 2nd ed., Cold Spring Harbor Laboratory, Cold Spring Harbor Laboratory Press, Cold Spring Harbor, N.Y., 1989).

In certain embodiments, the TERTC polynucleotides specifically proviso out polynucleotide sequences encoding hTERT deletion mutants described in Seimiya et al., supra.

The present invention also encompasses, in addition to the polynucleotides disclosed herein, (1) any nucleic acid that encodes a TERTC polypeptide of the invention; (2) the complement of any nucleic acid that encodes a TERTC polypeptide of the invention; (3) any polynucleotide that hybridizes to the complement of the sequences disclosed herein under highly stringent conditions, e.g., washing in 0.1×SSC/0.1% SDS at 68° C. (Ausubel et al., *Current Protocols in Molecular Biology*, Vol. I, Green Publishing Associates, Inc., and John Wiley & Sons, Inc., New York (1989) p. 2.10.3) and encodes a a functionally equivalent gene product; and/or (4) any polynucleotide that hybridizes to the complement of the sequences disclosed herein under less stringent conditions, such as moderately stringent conditions, e.g., washing in 0.2×SSC/0.1% SDS at 45° C. (Ausubel et al., 1989, supra) and encodes a functionally equivalent gene product.

The term "hybridizes under highly stringent conditions" is intended to describe conditions for hybridization and washing under which nucleotide sequences that are at least 60%, 65%, 70%, or preferably 75% identical to each other typically remain hybridized to each other. Such stringent conditions are known to those skilled in the art and can be found in *Current Protocols in Molecular Biology*, John Wiley & Sons, N.Y. (1989) pp. 6.3.1-6.3.6. A preferred, non-limiting example of stringent hybridization conditions are hybridization in 6× sodium chloride/sodium citrate ("SSC") at about 45° C. followed by one or more washes in 0.2×SSC, 0.1% SDS at 50-65° C. Preferably, an isolated polynucleotide of the invention that hybridizes under stringent conditions to the sequence of SEQ ID NO: 1 or a complement thereof.

The present invention also encompasses polynucleotide variants that are revealed from inter-species comparisons of homologs of the TERTC polynucleotides. As such, homologs of a TERTC polynucleotide of the invention that are found in other species and that display at least one of the functional characteristics of TERTC polypeptides are encompassed by the present invention.

Additionally, the present invention contemplates use of the TERTC polynucleotides of the invention to prevent and/or treat cellular transformation or cancer.

5.3 Recombinant Expression Vectors and Host Cells.

Another aspect of the invention pertains to vectors, preferably expression vectors, comprising a TERTC polynucleotide, nucleic acid sequence encoding a TERTC polypeptide, or a variant thereof. In a particular embodiment, an expression vector comprises a TERTC nucleic acid encoding a TERTC polypeptide of the invention (or a portion thereof).

As used herein, the term "vector" refers to a polynucleotide capable of transporting another nucleic acid to which it has been linked. One type of vector is a "plasmid", which refers to a circular double stranded DNA loop into which additional DNA segments can be introduced. Another type of vector is a viral vector, wherein additional DNA segments can be introduced into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses).

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the polynucleotide to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology*, (1990) Academic Press, San Diego, Calif., p. 185. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors comprising constitutive or inducible promoters directing the expression of either fusion or non-fusion proteins. Fusion vectors add a number of amino acids to a protein encoded therein, usually to the amino terminus of the recombinant protein. Such fusion vectors typically serve at least three purposes: 1) to increase expression of recombinant protein; 2) to increase the solubility of the recombinant protein; and/or 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., 1988, Gene 69:301-315) and pET 11d (Studier et al., Gene Expression Technology: Methods in Enzymology 185, Academic Press, San Diego, Calif. (1990) p. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, Gene Expression Technology: Methods in Enzymology 185, Academic Press, San Diego, Calif. (1990) p. 119-128). Another strategy is to alter the sequence of the nucleic acid to be inserted into an expression vector so that the individual codons for each amino acid are those preferentially utilized in E. coli (Wada et al., 1992, Nucleic Acids Res. 20:2111-2118). Such alteration of polynucleotides of the invention can be carried out by standard DNA synthesis techniques.

In another embodiment, the expression vector is a yeast expression vector. Examples of vectors for expression in yeast S. cerevisiae include pYepSec1 (Baldari et al., 1987, EMBO J. 6:229-234), pMFa (Kurjan and Herskowitz, 1982, Cell 30:933-943), pJRY88 (Schultz et al., 1987, Gene 54:113-123), pYES2 (Invitrogen Corp., San Diego, Calif.), and pPicZ (Invitrogen Corp., San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, Mol. Cell Biol. 3:2156-2165) and the pVL series (Lucklow and Summers, 1989, Virology 170:31-39).

In yet another embodiment, a TERTC nucleic acid of the invention is expressed in mammalian cells using a mammalian expression vector. Examples of mammalian expression vectors include pCDM8 (Seed, 1987, "An LFA-3 cDNA encodes a phospholipid-linked membrane protein homologous to its receptor CD2", Nature. 840-842) and pMT2PC (Kaufman et al., 1987, "Translational efficiency of polycistronic mRNAs and their utilization to express heterologous genes in mammalian cells", EMBO J. 6:187-193). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the TERTC nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733) and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, Proc Natl Acad Sci. 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374-379) and the α-fetoprotein promoter (Campes and Tilghman, 1989, Genes Dev. 3:537-546). In certain embodiments of the invention, it may be desirable to express only a low level of the TERTC polypeptide, and thus, promoters the activity of which that can be finely controlled are encompassed.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Accordingly, the present invention provides a host cell having an expression vector comprising a TERTC polynucleotide or a nucleic acid sequence encoding a TERTC polypeptide, or a variant thereof. A host cell can be any prokaryotic (e.g., E. coli) or eukaryotic cell (e.g., insect cells, yeast or mammalian cells). The invention also provides a method for making a TERTC polypeptide, comprising the steps of (a) culturing a cell comprising a recombinant TERTC polynucleotide under conditions that allow said TERTC polypeptide to be expressed by said cell; and isolating the expressed TERTC polypeptide.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a TERTC polypeptide of the invention. Accordingly, the invention further provides methods for producing a TERTC polypeptide of the invention using the host cells of the invention. In one embodiment, the method comprises culturing the host cell of invention (into which a recombinant expression vector encoding a TERTC polypeptide of the invention has been introduced) in a suitable medium such that the TERTC polypeptide is produced. In another embodiment, the method further comprises isolating the TERTC polypeptide from the medium or the host cell.

5.4 Antibodies to TERTC Polypeptides.

An isolated TERTC polypeptide of the invention, or a fragment thereof, can be used as an immunogen to generate antibodies using standard techniques for polyclonal and monoclonal antibody preparation.

In one embodiment, the invention provides substantially purified antibodies or fragments thereof, including human or non-human antibodies or fragments thereof, which antibodies or fragments specifically bind to a TERTC polypeptide of the invention comprising an amino acid sequence selected from the group consisting of: the amino acid sequence of SEQ ID NO:2; a fragment of at least 8 contiguous amino acid residues of the amino acid sequence of SEQ ID NO:2; an amino acid sequence which is at least 95% identical to the amino acid sequence of SEQ ID NO:2, wherein the percent identity is determined using the ALIGN program of the GCG software package with a PAM120 weight residue table, a gap length penalty of 12, and a gap penalty of 4; a fragment of at least 15 contiguous amino acid residues of the amino acid sequence of SEQ ID NO:2,; an amino acid sequence which is at least 95% identical to the amino acid sequence of SEQ ID NO:2, wherein the percent identity is determined using the ALIGN program of the GCG software package with a PAM120 weight residue table, a gap length penalty of 12, and a gap penalty of 4. In various embodiments, the substantially purified antibodies of the invention, or fragments thereof, can be human, non-human, chimeric and/or humanized antibodies.

The term "antibody" as used herein refers to immunoglobulin molecules and immunologically active portions of immunoglobulin molecules, i.e., molecules that comprise an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally comprises the polypeptide. Examples of immunologically active portions of immunoglobulin molecules include F(ab) and F(ab')2 fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that comprise only one species of an antigen binding site capable of immunoreacting with a particular epitope.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S. Pat. No. 4,816,397, which are incorporated herein by reference in their entirety). Humanized antibodies are antibody molecules from non-human species having one or more complementarity determining regions (CDRs) from the non-human species and a framework region from a human immunoglobulin molecule (see, e.g., Queen, U.S. Pat. No. 5,585,089, which is incorporated herein by reference in its entirety). Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc Natl Acad Sci. 84:3439-3443; Liu et al., 1987, J. Immunol. 139:3521-3526; Sun et al., 1987, Proc Natl Acad Sci. 84:214-218; Nishimura et al., 1987, Cancer Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

An antibody directed against a TERTC polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

In further embodiments, the invention provides an antibody that immunospecifically binds to a TERTC polypeptide when bound to a binding partner, such as telomerase RNA, chromosomal DNA, telomeric DNA or the ends of chromosomes, and 14-3-3 proteins. In yet another embodiment, the invention provides an antibody that immunospecifically binds to a TERTC polypeptide when bound to a binding partner; wherein said antibody does not bind to said polypeptide when not bound to said binding partner.

5.5 Functional Analysis of the TERTC Polypeptides.

According to the invention, the TERTC polypeptides lack or exhibit greatly reduced catalytic activity, and while expressed in a cell that contains functional telomerase, the TERTC polypeptides do not inhibit the activity of the cellular telomerase.

Telomerase catalytic activity may be processive or nonprocessive. Processive telomerase catalytic activity occurs when a telomerase ribonuclepoprotein adds multiple repeats to a primer or telomerase before the DNA is released by the enzyme complex (see, e.g., Morin, 1989, Cell 59:521 and Morin, 1997, Eur. J. Cancer 33:750). Nonprocessive activity occurs when telomerase adds a partial, or only one, repeat to a primer and is then released (see Morin, 1997, supra). In various embodiments of the invention, the TERTC polypeptides lack processive or nonprocessive telomerase catalytic activity.

Processive telomerase catalytic activity can be assayed by a variety of methods, including the assay described in Morin (1989, Cell 59:521), the TRAP assay (U.S. Pat. No. 5,629,154; see also, PCT publication WO 97/15687, PCT publication WO 95/13381; Krupp et al. Nucleic Acids Res., 1997, 25: 919; Wright et al., 1995, Nuc. Acids Res. 23:3794), the "dot blot immunoassay" (U.S. Pat. No. 5,968,506), and other assays (e.g., Tatematsu et al., 1996, Oncogene 13:2265). The TRAPeze.TM. Kit (Oncor, Inc., Gaithersburg, Md.) may also be used. The telomerase substrate used in these assays may have a natural telomere sequence, or may be have a synthetic oligonucleotide with a different sequence (see, e.g., Morin, 1989, Cell 59:521; Morin, 1991, Nature 353:454-56).

The activity of telomerase in cells can be estimated by the change in telomere length after a number of cell divisions. Telomeric DNA consists of small, tandemly repeated DNA sequences (e.g., human repeat sequence, TTAGGG). These G-rich sequences are highly conserved during evolution. They appear to be involved in determining the proliferative capacity and lifespan of both normal and malignant cells. Determinations of telomere length may provide important information about normal cell aging. One method described involves the synthesis of DNA complementary to the telomeres of genomic DNA. The synthesized DNA can be labeled or unlabeled, and the length of this DNA can be determined by techniques known in the art. See, for example, the Telo TTAGGG Telomere Length Assay Kit (Roche).

Another method is known as terminal restriction fragments (TRF) analysis. In this method, the genomic DNA is digested with a restriction enzyme with a four-base recognition sequence (e.g. AluI, HinfI, MspI, RsaI, and Sau3A, used individually or in combination), which results in the production of short fragments of DNA, except for telomeric DNA which lacks these four base sequences. The DNA is then electrophoresed and a Southern blot performed by hybridizing the DNA to a radiolabeled probe, such as (TTAGGG)$_3$ (SEQ ID NO:3) or (CCCTAA)$_3$ (SEQ ID NO:4). The telomeric smears can then be visualized by autoradiography, and mean lengths of terminal restriction fragments calculated from densitometric scans using computer programs known in the art. See for example, Harley et al., 345 Nature 458, 1990.

According to the invention, expressing a TERTC polypeptide in a cancer cell can lead to telomere dysfunction, characterized by the formation of anaphase bridges, chromosome end-to-end fusion. Any techniques known in the art for staining chromosomes, and visualizing chromosomal structures can be used to study the effects of TERTC polypeptides in cancer cells.

Cellular senescence which can be induced by hydrogen peroxide can be assayed by any methods known in the art, including but not limited to, β-galactosidase activity assay (Dimri et al., (1995) Proc. Natl. Acad. Sci. USA. 92, 9363-9367).

Most eukaryotic cells have the ability to self-destruct by activation of an intrinsic cellular suicide program referred to as programmed cell death or apoptosis. According to the invention, expressing a TERTC polypeptide in a cancer cell can lead to apoptosis. The process of apoptosis involves a cascade of cytoplasmic and nuclear events that result in a series of morphological changes, and eventually cause the demise of the cell. Apoptosis is characterized by distinct biochemical and morphological changes exhibited by cells undergoing programmed cell death, including DNA fragmentation, plasma membrane blebbing, and cell volume shrinkage. At the molecular level, activation of one or more aspartate-specific, cysteine proteases (caspases) is proposed to be the critical signal required to carry out apoptotic cell death (Yang et al., American Journal of Pathology, 152(2): 379-389, 1998).

The caspases, also known as ICE (IL-1 β-converting enzyme)-like proteases, can be divided into three subclasses: ICE/CED3 family, CPP32/Yama family and the Ich/Nedd2 family (Duan et al., J. Biol. Chem., 271:1621-1625, 1996). All family members share a high level of amino acid sequence homology with ICE, and contain a conserved QACRG (SEQ ID NO:5) pentapeptide in which the cysteine participates in catalysis (Nicholson, Nature Biotech., 14:297-301, 1996). Furthermore, all of these proteases are reported to require an aspartic acid residue at the substrate P1 position (Janicke et al., The EMBO J., 15(24):6969-6978, 1996).

CPP32 (Caspase 3) has been identified as one of the proteases that cleaves poly(ADP-ribose) polymerase (PARP) (Schlegel et al., J. Biol. Chem., 271:1841-1844, 1996; Nicholson et al., Nature, 376:37-42, 1995). PARP is one of the enzymes associated with DNA repair. Cleavage of the approximately 116 kDa PARP protein into fragments of about 89 kd and about 27 kd has been reported to contribute to the DNA fragmentation that is characteristic of apoptosis (Kayalar et al., Proc. Natl. Acad. Sci. USA, 93:2234-2238, 1996).

A cell in apoptosis can also be identified by nuclear chromatin condensation, nuclear shrinkage, ordered cleavage of the nuclear DNA, compactness of cytoplasmic organelles, and the appearance of an irregular plasma membrane (Kerr, J. F. et al., Brit. J. Cancer 26:2392-57 (1972).

A discrete change which occurs early, before nuclear alterations, is the redistribution of phosphatidylserine from the plasma membrane inner leaflet to become exposed at the cell surface. The externalization of phosphatidylserine is known to occur very early during apoptosis. Assays have incorporated the use of annexin V, a member of a family of calcium-dependent phospholipid-binding proteins, that possesses strong affinity for phosphatidylserine. Andree, H. A. et al., J. Biol. Chem. 265:4923-4928 (1990). Since phosphatidylserine translocation occurs early in apoptosis when cell membrane integrity is still intact, flow cytometric analysis using fluorescein isothiocyanate- labeled annexin V is now widely used as a quantitative measure of early apoptosis. Homburg, C. H. et al., Blood 85:532-540 (1995); Koopman, G. et al., Blood 84:1415-1420 (1994); Vanags, D. M. et al., J. Biol. Chem. 271:31075-31085 (1996). See also U.S. Pat. No. 5,939,267.

Other assays that identify the end stages of apoptosis that include gel electrophoresis DNA fragmentation assays, DNA 3'-OH end labeling, electron microscopy, and hematoxylin and eosin staining (Hill, I. E. et al., Brain Res. 676:398-403 (1995); Maiese, K., Clinical Neuropharm. 21:1-7 (1998); Vincent, A. M. et al., J. Neurosci Res. 50:549-564 (1997)) can also be used.

The identification of any of the above exemplary apoptosis molecular markers is an indication that the cell is undergoing or has undergone apoptosis. Accordingly, without being limiting, the above markers and techniques can be used to determine whether cancer cells expressing TERTC polypeptides or treated with TERTC polynucleotides are undergoing apoptosis.

5.6 Uses and Methods of the Invention.

The TERTC polynucleotides, TERTC polypeptides and variants thereof, TERTC polypeptide analogs described herein can be used in screening assays; and methods of treatment (e.g., therapeutic and prophylactic).

5.6.1 TERTC Assays.

In one embodiment, the invention provides assays for screening TERTC analogs, peptidomimetics or test compounds which display similar characteristics of TERTC polypeptides, such as C27. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145). The functional characteristics of TERTC analogs can be determined by methods described in the example section for testing C27 and/or methods known in the art for determining telomerase activity and cancer cell phenotype.

In another embodiment of the invention, a TERTC polypeptide of the inventions can be used as "bait proteins" in a two-hybrid assay or three hybrid assay (see, e.g., U.S. Pat. No. 5,283,317; Zervos et al., 1993, Cell 72:223-232; Madura et al., 1993, J Biol Chem. 268:12046-12054; Bartel et al., 1993, BioTechniques 14:920-924; Iwabuchi et al., 1993, Oncogene 8:1693-1696; and PCT Publication No. WO 94/10300), to identify other proteins, which bind to or interact with the TERTC polypeptide of the invention and modulate activity of the polypeptide of the invention. Such binding proteins, for example TRF2, are also likely to be involved in mediating the senescence-like effect of TERTC polypeptides or the propagation of signals to the cells to undergo apoptosis. Other examples of proteins that may interact with the C-terminus of TERT include components of the DNA damage response machinery, such as Ku, ATM, RAD50, MRE11 and NBS1 which are located on human telomeres (Wong et al., (2000) Nat. Genet. 26, 85-88; Blackburn, E. H. (2001) Cell 106, 661-673; Peterson et al., (2001) Nat. Genet. 27, 64-67; Samper et al., (2000) EMBO Reports 1, 244-252; Lim et al.,(2000) Nature 404, 613-617; and Zhu et al., (2000) Nat. Genet. 25, 347-352.). The use of these proteins in a binding or competition assay in conjunction with a TERTC polypeptide is also contemplated.

In various embodiments, the present invention provides the measurement of TERTC polypeptides and gene products (e.g., mRNA), and the uses of such measurements in clinical applications. The measurement of TERTC polypeptides and gene product of the invention can be valuable in in monitoring the effect of a therapeutic treatment on a subject. In specific embodiments, the present invention provides a method for monitoring the effectiveness of treatment of a subject with an agent (e.g., a TERTC peptidomimetic, TERTC variant polypeptide, TERTC nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

When a TERTC polypeptide or gene product is present in the cytoplasm, the antibody or nucleic acid probe of the invention can be introduced inside the cell, for example, by making the cell membrane permeable. Through the use of such a procedure, it is possible to determine not only the presence of a TERTC polypeptide or gene product, or variants, but also the distribution in a cell, tissue, or organ of interest. Using the present invention, those of ordinary skill will readily perceive that any of a wide variety of histological methods (such as staining procedures) can be modified in order to achieve such in situ detection.

Immunoassays for TERTC polypeptide or gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying TERTC gene products or conserved variants or peptide fragments thereof, and detecting the bound antibody by any of a number of techniques well-known in the art.

One of the ways in which the TERTC polypeptide-specific antibody can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.); Voller et al., 1978, J. Clin. Pathol. 31:507-520; Butler, 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). Detection may also be accomplished using any of a variety of other immunoassays. For example, by radioactively labeling the antibodies or antibody fragments, it is possible to detect TERTC peptides through the use of a radioimmunoassay (RIA) (See, e.g., Weintraub, B., *Principles of Radioimmunoassays, Seventh Training Course on Radioligand Assay Techniques*, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound and a bioluminescent compound. Any of numerous immunoassays can be used in the practice of the instant invention. Antibodies, or antibody fragments comprising the binding domain, are known in the art or can be obtained by procedures standard in the art such as those described in Harlow and Lane, *Antibodies: A Laboratory Manual*, Cold Spring Harbor Laboratory, 1988.

In other embodiments, the invention provides a method for identifying a protein that binds a TERTC polypeptide comprising the steps of (a) contacting said TERTC polypeptide with a positionally addressable array comprising a plurality of proteins, with each protein being at a different position on a solid support; and (b) detecting binding of said TERTC polypeptide to a protein on said array. Also included is a method for identifying an analyte that binds a complex comprising a TERTC polynucleotide or TERTC polypeptide comprising the steps of (a) contacting said complex with said analyte under conditions that allow said analyte to bind said complex; and (b) detecting binding of said TERTC polypeptide to said analyte; wherein said analyte binds to said TERTC polypeptide when bound to said binding partner, and does not bind to said TERTC polypeptide when not bound to said binding partner.

5.6.2 Treatment of Diseases

The present invention encompasses methods for the prevention and/or treatment of proliferative disorders, including but not limited cancer. More particularly, the present invention relates to uses of TERTC polynucleotides, polypeptides, and analogs for the prevention and management of cancer, preferably cancers with reactivated telomerase. TERTC polynucleotides, TERTC polypeptides, and analogs thereof, can be used to modulate the development and progression of non-cancerous cell-proliferative disorders such as, but not limited to, deregulated proliferation (e.g., hyperdysplasia, hyper-IgM syndrome, or lymphoproliferative disorders), cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

Cancer describes a disease state in which a carcinogenic agent or agents causes the transformation of a healthy cell into an abnormal cell, which is followed by an invasion of adjacent tissues by these abnormal cells, and which may be followed by lymphatic or blood-borne spread of these abnormal cells to regional lymph nodes and/or distant sites, i.e., metastasis. Abnormal cell regulation may lead to tumor growth such that the tissue mass is increased because of greater cell numbers as a result of faster cell division and/or slower rates of cell death. Tumors may be malignant or non-malignant.

The invention contemplates uses of TERTC polynucleotides, TERTC polypeptides and analogs to treat cancer, i.e., to induce senescence and/or apoptosis in cancer cells, inhibit the replication of cancer cells, inhibit the spread of cancer, decrease tumor size, lessen or reduce the number of cancerous cells in the body, or ameliorate or alleviate the symptoms of the disease caused by the cancer. Such treatment is considered therapeutic if there is a decrease in mortality and/or morbidity, or a decrease in disease burden manifest by reduced numbers of malignant cells in the body.

The invention contemplates uses of TERTC polynucleotides, polypeptides, and analogs to prevent cancer, i.e., to prevent the occurrence or recurrence of the disease state of cancer. As such, a treatment that impedes, inhibits, or interferes with metastasis, tumor growth, or cancer proliferation has preventive activity.

TERTC polynucleotides, TERTC polypeptides, and variants and analogs thereof, can also be used to modulate the development and progression of cancers such as, but not limited to, neoplasms, tumors, carcinomas, sarcomas, adenomas or myeloid lymphoma tumors, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon sarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hematoma, bile duct carcinoma, melanoma, choriocarcinoma, semicoma, embryonal carcinoma, Wilms' tumor, cervical cancer, testicular tumor, lung carcinoma, small cell carcinoma, bladder carcinoma, epithelial carcinoma, glioma, astrocytoma, medulloblastoma, craniopharyngioma, ependynoma, pinealoma, hemangioblastoma, retinoblastoma), leukemias, (e.g. acute lymphocytic leukemia), acute myclocytic leukemia (myclolastic, promyelocytic, myelomonocytic, monocytic and erythroleukemia), chronic leukemias (chronic myclocytic (granulocytic) leukemia and chronic lymphocytic leukemia), or polycythemia vera, or lymphomas (Hodgkin's disease and non-Hodgkin's diseases), multiple myelomas and Waldenström's macroglobulinemia.

5.6.3 Gene Therapy.

In one embodiment, gene therapy approaches can be used in accordance with the present invention to obtain the expression of a TERTC polynucleotide in a cancer cell. Gene therapy refers to therapy performed by the administration to a subject of an expressed or expressible nucleic acid. Accordingly, the present invention provides for a method for treating or preventing a proliferative disorder including cancer comprising administering to a patient in need thereof an effective amount of a mammalian expression vector comprising a TERTC polynucleotide, or a variant thereof. In further embodiments, the polynucleotide encodes a TERTC polypeptide, or TERTC variant.

Any composition described for administration by gene therapy can also be useful, apart from gene therapy approaches, for in vitro or ex vivo manipulations.

Any of the methods for gene therapy available in the art can be used in accordance with the present invention (See, e.g., Goldspiel et al., 1993, Clinical Pharmacy 12:488-505; Grossman and Wilson, 1993, Curr. Opin. in Genetics and Devel. 3:110-114; Salmons and Gunzberg, 1993, Human Gene Therapy 4:129-141; Morgan and Anderson, 1993, Ann. Rev. Biochem. 62:191-217; Mulligan, 1993, Science 260:926-932; Tolstoshev, 1993, Ann. Rev. Pharmacol. Toxicol. 32:573-596; and Clowes et al., 1994, J. Clin. Invest. 93:644-651; Kiem et al., 1994, Blood 83:1467-1473, each of which is incorporated herein by reference). Gene therapy vectors can be administered to a subject systemically or locally by, for example, intravenous injection (See, e.g., U.S. Pat. No. 5,328,470) or by stereotactic injection (See, e.g., Chen et al., 1994, Proc Natl Acad Sci. 91:3054-57). Synthetic genes, the in vitro or in vivo transcription and translation of which results in the production of a TERTC polypeptide, for example, may be constructed by techniques well known in the art.

A pharmaceutical preparation of the gene therapy vector can comprise a gene therapy vector in an acceptable diluent, or can comprise a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The present invention encompasses vectors comprising a nucleic acid encoding a TERTC polypeptide of the invention, or the complement thereof. In one embodiment, a TERTC polynucleotide of the invention to be introduced for purposes of gene therapy comprises an inducible promoter operably linked to the coding region in the antisense orientation, such that expression of the nucleic acid can be controlled using an appropriate inducer or inhibitor of transcription. In another embodiment, the vector comprises a promoter which expresses the cloned construct constitutively. In a further embodiment, the promoter can be down-regulated by a suppressor molecule. Alternatively, the vector comprises a promoter, such that an inducing molecule initiates or increases expression of the cloned TERTC polynucleotide. In a preferred embodiment, the vector comprises a cell-specific promoter. In another preferred embodiment, the vector comprises a disease-specific promoter, such that expression is largely limited to diseased tissues or tissues surrounding diseased tissues.

Gene therapy involves introducing a gene construct to cells in tissue culture or in vivo. Methods for introduction of polynucleotides of the invention to cells in vitro include, but are not limited to, electroporation, lipofection, calcium phosphate-mediated transfection, and viral infection. Usually, the method of transfer includes the transfer of a selectable marker to the cells, after which the cells are placed under selection to isolate the cells which have taken up and express the transferred gene. The transfected cells then an be administered to a subject.

An expression construct can be delivered directly into a subject. In one embodiment, the polynucleotides of the invention can be injected directly into the target tissue or cell derivation site. Alternatively, a subject's cells are first transfected with an expression construct in vitro, after which the transfected cells are administered back into the subject (i.e., ex vivo gene therapy). Accordingly, the polynucleotides of the invention can be delivered in vivo or ex vivo to target cells. Several methods have been developed for delivering the polynucleotides of the invention to target cells or target tissues.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject. In another embodiment, the polynucleotides of the invention can be introduced into the target tissue as an implant, for example, in a polymer formulation (See, e.g., U.S. Pat. No. 5,702,717). In another embodiment, the polynucleotides of the invention can be targeted to the desired cells or tissues.

In a particular embodiment, a vector is introduced in vivo such that it is taken up by a cell and directs the transcription of an TERTC nucleic acid of the invention. Such a vector can remain episomal or can become chromosomally integrate. Expression vectors can be plasmid, viral, or others known in the art, that can be used to replicate and/or express the cloned nucleotide sequence encoding a TERTC polynucleotide in a target mammalian cell. A variety of expression vectors useful for introducing into cells the polynucleotides of the inventions are well known in the art (See, e.g., Promega™ catalogue, 2001; Stratagene™ catalogue, 2001). Expression constructs can be introduced into target cells and/or tissues of a subject using vectors which include, but are not limited to adenovirus, adeno-associated virus, retrovirus and herpes virus vectors, in addition to other particles that introduce DNA into cells, such as liposomes.

A polynucleotide of the invention can be expressed using any promoter known in the art capable of expression in mammalian, preferably human cells. Such promoters can be inducible or constitutive. These promoters include, but are not limited to, a casein promoter (Cerdan et al., 1998, "Accurate spatial and temporal transgene expression driven by a 3.8-kilobase promoter of the bovine beta-casein gene in the lactating mouse mammary gland", Mol Reprod Dev 49(3):236-45), whey acid promoter (Doppler et al., 1991, "Lactogenic hormone and cell type-specific control of the whey acidic protein gene promoter in transfected mouse cells", Mol Endocrinol 5:1624-1632), SV40 early promoter region (Bernoist and Chambon, 1981, Nature 290:304-310), the promoter compriseed in the 3' long terminal repeat of Rous sarcoma virus (Yamamoto et al., 1980, Cell 22:787-797), the herpes thymidine kinase promoter (Wagner et al., 1981, Proc Natl Acad Sci. 78:1441-1445), and the regulatory sequences of the metallothionein gene (Brinster et al., 1982, Nature 296:39-42).

In another embodiment, an TERTC polynucleotide comprises an appended group such as a peptide (e.g., for targeting host cell receptors in vivo), or an agent that facilitates transport across the cell membrane (See, e.g., Letsinger et al., 1989, Proc Natl Acad Sci. 86:6553-6556; Lemaitre et al., 1987, Proc Natl Acad Sci. 84:648-652; PCT Publication No. WO 88/09810) or the blood-brain barrier (See, e.g., PCT Publication No. WO 89/10134).

Any type of plasmid, cosmid, YAC or viral vector can be used to prepare the recombinant construct. Alternatively, vectors can be used which selectively target a tissue or cell type, e.g., viruses which infect breast cells. Further specificity can be realized by using a tissue-specific or cell-specific promoter in the expression vector.

In a specific embodiment, an expression vector is administered directly in vivo, where the vector is expressed to produce the encoded product. This can be accomplished by any of numerous methods known in the art, e.g., by placing a nucleic acid of the invention in an appropriate expression vector such that, upon administration, the vector becomes intracellular and expresses a TERTC antisense oligonucleotide. Such vectors can be internalized by using, for example, a defective or attenuated retroviral vector or other viral vectors that can infect mammalian cells (See, e.g., U.S. Pat. No. 4,980,286).

Alternatively, an expression construct comprising a nucleic acid of the invention can be injected directly into a target tissue as naked DNA. In another embodiment, an expression construct comprising a nucleic acid of the invention can be introduced intracellularly using microparticle bombardment, for example, by using a Biolistic gene gun (Dupont™). In another embodiment, an expression construct comprising a nucleic acid of the invention can be coated with lipids, or cell-surface receptors, or transfecting agents, such that encapsulation in liposomes, microparticles, or microcapsules facilitates access to target tissues and/or entry into target cells. In yet another embodiment, an expression construct comprising a nucleic acid of the invention is linked to a polypeptide that is internalized in a subset of cells or is targeted to a particular cellular compartment. In a further embodiment, the linked polypeptide is a nuclear targeting sequence which targets the vector to the cell nucleus. In another further embodiment, the linked polypeptide is a ligand that is internalized by receptor-mediated endocytosis in cells expressing the respective receptor for the ligand (See, e.g., Wu and Wu, 1987, J. Biol. Chem. 262:4429-4432).

In another embodiment, nucleic acid-ligand complexes can be formed such that the ligand comprises a fusogenic viral peptide which disrupts endosomes, thereby allowing the nucleic acid to avoid lysosomal degradation. In another embodiment, a nucleic acid of the invention can be targeted in vivo via a cell-specific receptor resulting in cell-specific uptake and expression (See, e.g., International Patent Publications WO 92/06180, WO 92/22635, WO 92/20316, WO 93/14188, and WO 93/2022. In yet another embodiment, a nucleic acid of the invention is introduced intracellularly and, by homologous recombination, can transiently or stably be incorporated within the host cell DNA, which then allows for its expression, (Koller and Smithies, 1989, Proc Natl Acad Sci. 86:8932-8935; Zijlstra et al., 1989, Nature 342: 435-438).

Greater detail about retroviral vectors is available in Boesen et al., 1994, Biotherapy 6:291-302, which describes the use of a retroviral vector to deliver the mdr1 gene to hematopoietic stem cells.

Many other viral vectors can also be used for gene therapy approaches in accordance with the invention. For example, adenoviruses are useful for delivering gene constructs to respiratory epithelia. Other targets for adenovirus-based delivery systems are the liver, the central nervous system, endothelial cells, and muscle cells. Moreover, adenoviruses are able to infect non-dividing cells (See, e.g., Rosenfeld et al., 1991, Science 252:431-434; Rosenfeld et al., 1992, Cell 68:143-155; Mastrangeli et al., 1993, J. Clin. Invest. 91:225-234; Kozarsky and Wilson, 1993, Curr. Opin. Genetics Develop. 3:499-503; Bout et al., 1994, Human Gene Therapy 5:3-10; PCT Publication No. WO 94/12649; and Wang et al., 1995, Gene Therapy 2:775-783).

Adeno-associated virus can also be used in accordance with the gene therapy approaches of the present invention (See, e.g., Walsh et al., 1993, Proc. Soc. Exp. Biol. Med. 204:289-300; U.S. Pat. No. 5,436,146).

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral or bacteriophage vector comprising the polynucleotides, cell fusion, chromosome-mediated gene transfer, microcell-mediated gene transfer, and spheroplast fusion. Numerous techniques are known in the art for the introduction of foreign genes into cells (See, e.g., Maniatis et al., 1989; *Current Protocols in Molecular Biology*, John Wiley & Sons, 2000; Loeffler and Behr, 1993, Meth. Enzymol. 217:599-618; Cohen et al., 1993, Meth. Enzymol. 217:618-644; Cline, 1985, Pharmacol. Ther. 29:69-92) and can be used in accordance with the present invention. In a preferred embodiment, the technique stably transfers a nucleic acid of the invention to a target cell, such that the nucleic acid is inherited by the cell's progeny.

The resulting recombinant cells can be delivered to a subject by various methods known in the art, and the skilled artisan would appreciate appropriate modes of administration. For example, intravenous administration may be the preferred mode of administration for recombinant hematopoietic stem cells. Similarly, the number of recombinant cells to be administered to a subject can be determined by one skilled in the art, and would include a consideration of factors such as the desired effect, the disease state, and the mode of administration.

5.6.4 Combination Therapies

The administration of a TERTC polypeptide can potentiate the effect of anti-cancer agents. In a particular embodiment, the invention provides that TERTC polypeptides can sensitize cancer cells to oxidative stress, prevent or delay development of cellular resistance to anticancer agents that create oxidative stress, or reduce cellular resistance to anticancer agents that generate oxidative stress. In preferred embodiments, the invention encompasses the use of combination therapy to treat cancer. These combination therapies can also be used to prevent cancer, prevent the recurrence of cancer, or prevent the spread or metastasis or cancer.

Combination therapy also includes, in addition to administration of a TERTC polypeptide, the use of one or more molecules, compounds or treatments that aid in the prevention or treatment of cancer (i.e., anticancer drugs), which molecules, compounds or treatments includes, but is not limited to, chemoagents, immunotherapeutics, cancer vaccines, anti-angiogenic agents, cytokines, hormone therapies, gene therapies, and radiotherapies. In specific embodiments, the TERTC polypeptide is used in conjunction with an anticancer drug that generate oxidative stress, e.g., through the generation of reactive oxygen species.

In one embodiment, one or more anticancer drug, in addition to a TERTC polypeptide, is administered to treat a cancer patient. A chemoagent (or "chemotherapeutic agent") is a type of anticancer drug that refers to any molecule or compound that assists in the treatment of tumors or cancer. Examples of chemoagents contemplated by the present invention include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, Bacillus Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gemcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or variants thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

The invention, therefore, contemplates the use of one or more TERTC polypeptides, which is administered prior to, subsequently, or concurrently with doses of chemoagents, for the prevention or treatment of cancer.

In another embodiment, a TERTC polypeptide is administered in combination with one or more immunotherapeutic agents, such as antibodies and immunomodulators, which includes, but is not limited to, Herceptin®, Retuxan®, OvaRex, Panorex, BEC2, IMC-C225, Vitaxin, Campath I/H, Smart M195, LymphoCide, Smart I D10, and Oncolym, rituxan, rituximab, gemtuzumab, or trastuzumab.

In another embodiment, a TERTC polypeptide is administered in combination with one or more anti-angiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), or any fragments, family members, or variants thereof, including pharmaceutically acceptable salts thereof.

In another embodiment, a TERTC polypeptide is administered in combination with a regimen of radiation.

In another embodiment, a TERTC polypeptide is administered in combination with one or more cytokines, which includes, but is not limited to, lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1 BBL, endothelial monocyte activating protein or any fragments, family members, or variants thereof, including pharmaceutically acceptable salts thereof.

In yet another embodiment, a TERTC polypeptide is administered in combination with a cancer vaccine. Examples of cancer vaccines include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-specific antigens (e.g., BAGE, GAGE-1, GAGE-2, MAGE-1, MAGE-3, N-acetylglucosaminyltransferase-V, p15), mutated antigens that are tumor-specific (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma)). For human tumor antigens recognized by T cells, see generally Robbins and Kawakami, 1996, Curr. Opin. Immunol. 8:628-36. Cancer vaccines may or may not be purified preparations.

In yet another embodiment, a TERTC polypeptide is used in association with hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

5.6.5 Pharmaceutical Compositions.

Since expression of a TERTC polynucleotide or introduction of a TERTC polypeptide can have significant therapeutic responses in a patient with a proliferative disorder, the invention provides useful pharmaceutical compositions, treatment courses, and modes of delivery. Accordingly, in one embodiment, a pharmaceutical composition comprises a polynucleotide or polypeptide of the invention, and variants thereof, which refers to any pharmaceutically acceptable homologue, analogue, or fragment corresponding to the pharmaceutical composition of the invention. In another embodiment, the present invention provides for a pharmaceutical composition that comprises a TERTC polypeptide and a pharmaceutically acceptable carrier.

The phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other generally recognized pharmacopeia for use in animals, more particularly for use in humans.

The carrier can be a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic lipids, including, but not limited to N-(1(2,3-dioleyloxy)propyl)-N,N,N-trimethylammonium chloride (DOTMA) and diolesylphosphotidylethanolamine (DOPE). Liposomes are also suitable carriers for the antisense oligonucleotides of the invention. Such compositions should comprise a therapeutically effective amount of the compound, together with a suitable amount of carrier so as to provide the form for proper administration to the patient. The formulation should suit the mode of administration.

Pharmaceutically acceptable salts are prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such compositions should comprise a therapeutically effective amount of the compound, together with a suitable amount of carrier so as to provide an appropriate formulation for administration to a patient. For example, oral administration requires enteric coatings to protect the antagonist from degradation within the gastrointestinal tract. In another example, the antagonist may be administered in a liposomal formulation to facilitate transport in circulatory system, effect delivery across cell membranes to intracellular sites, and shield the antagonist from degradative enzymes.

In another embodiment, a pharmaceutical composition comprises a TERTC polypeptide and one or more therapeutic agents and a pharmaceutically acceptable carrier. In a particular embodiment, the pharmaceutical composition comprises a TERTC polypeptide and one or more cancer therapeutic agents and a pharmaceutically acceptable carrier.

In a further embodiment, a pharmaceutical composition, comprising a TERTC polypeptide, with or without other therapeutic agents, and a pharmaceutically acceptable carrier, is at an effective dose.

The compositions of the invention can be formulated as neutral or salt forms. Pharmaceutically acceptable salts include those formed with free amino groups, such as for example, those derived from hydrochloric, phosphoric, acetic, oxalic, and tartaric acids, and those formed with free carboxyl groups, such as for example, those derived from sodium, potassium, ammonium, calcium, ferric hydroxides, isopropylamine, triethylamine, 2-ethylamino ethanol, histidine, and procaine.

In a preferred embodiment, the composition is formulated in accordance with routine procedures as a pharmaceutical composition adapted for subcutaneous injection or intravenous administration to humans. Typically, compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

The polynucleotides, polypeptides, and analogs of the invention can be incorporated into pharmaceutical compositions suitable for administration. Such compositions typically comprise the polynucleotide, protein, or antibody, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the pharmaceutical compositions of the invention is contemplated.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and additional polynucleotides, polypeptides, and analogs of the invention.

Selection of a preferred effective dose can be determined by a skilled artisan based upon the consideration of factors which will be known to one of ordinary skill in the art. Such factors include the particular form of a TERTC polypeptide and its pharmacokinetic parameters such as bioavailability, metabolism and half-life, which is established during the development procedures typically employed in obtaining regulatory approval of a pharmaceutical compound. Further factors that can be used to determine an effective dose include the disease to be treated, the benefit to be achieved in a patient, the patient's body mass, the patient's immune status, the route of administration, whether administration of a TERTC polypeptide and/or combination therapeutic agent is acute or chronic, concomitant medications, and other factors known by the skilled artisan to affect the efficacy of administered pharmaceutical agents.

In one embodiment, the pharmaceutical composition comprises a TERTC polynucleotide at a dose of about 0.01 to 0.1, 0.1 to 1, 1 to 5, or 6 to 10 mg/kg/day; and a pharmaceutically acceptable carrier. The actual amount of any particular polynucleotide administered can depend on several factors, such as the type of disease, the toxicity of the antisense oligonucleotide to normal cells of the body, the rate of uptake of the TERTC polynucleotide by tumor cells, and the weight and age of the individual to whom the TERTC polynucleotide is administered. The skilled artisan will appreciate the factors that may interfere with the action or biological activity of the TERTC polynucleotide in vivo, an effective amount of the TERTC polynucleotide can be determined empirically by routine procedures, including, for example, via clinical trials.

In another embodiment, the pharmaceutical compositions of the invention comprise a TERTC polynucleotide at a particularly high dose, which ranges from about 10 to 50 mg/kg/day. In a specific embodiment a particularly high dose of TERTC polynucleotide, ranging from 11 to 15, 16 to 20, 21 to 25, 26 to 30, 31 to 35, 36 to 40, 41 to 45, or 46 to 50 mg/kg/day, is administered during a treatment cycle.

A preferred effective dose of a TERTC polynucleotide can be determined by a skilled artisan, especially given that several TERTC polynucleotide compounds are currently undergoing clinical trials. These routine trials can establish the particular form of TERTC polynucleotide to be administered, an appropriate delivery route, and a particular TERTC polynucleotide's pharmacokinetic parameters such as bioavailability, metabolism, and half-life. Other factors typically considered during the course of a clinical trial are the patient's body mass, the patient's immune status, the disease to be treated, the benefit to be achieved in a patient, the route of administration, whether administration of an TERTC polynucleotide and/or combination therapeutic agent is acute or chronic, concomitant medications, and other factors known by the skilled artisan to affect the efficacy of administered pharmaceutical agents.

5.6.6 Modes of Administration.

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. A pharmaceutical composition of the invention is formulated to be compatible with its intended route of administration. Examples of routes of administration include parenteral, e.g., intravenous, intramuscular, intraperitoneal, intraorbital, intracapsular, intraspinal, intrasternal, intra-arterial, intradermal, subcutaneous, oral (e.g., inhalation), transdermal (topical), transmucosal, and rectal administration. The skilled artisan can appreciate the specific advantages and disadvantages to be considered in choosing a mode of administration.

Multiple modes of administration are encompassed by the invention. For example, a TERTC polypeptide is administered by subcutaneous injection, whereas a combination therapeutic agent is administered by intravenous infusion.

A TERTC polypeptide can be administered before, during, and/or after the administration of one or more therapeutic agents.

Moreover, administration of one or more species of TERTC polypeptide, with or without other therapeutic agents, may occur simultaneously (i.e., co-administration) or sequentially. In one embodiment, a TERTC polypeptide is first administered to increase sensitivity of a tumor to subsequent administration of a cancer therapeutic agent or irradiation therapy. In another embodiment, the periods of administration of one or more species of a TERTC polypeptide, with or without other therapeutic agents may overlap. For example, a TERTC polypeptide is administered for 14 days, and a second therapeutic agent is introduced beginning on the seventh day of TERTC polypeptide treatment, and treatment with the second therapeutic agent continues beyond the 14-day TERTC polypeptide treatment.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide, for example. The parenteral preparation can be enclosed in ampules, disposable syringes or multiple dose vials made of glass or plastic.

Pharmaceutical compositions adapted for parenteral administration include, but are not limited to, aqueous and non-aqueous sterile injectable solutions or suspensions, which may contain antioxidants, buffers, bacteriostats and solutes that render the compositions substantially isotonic with the blood of an intended recipient. Such compositions may also comprise water, alcohols, polyols, glycerine and vegetable oils, for example. Compositions adapted for parenteral administration can be packaged in unit-dose or multi-dose containers (e.g., sealed ampules and vials). These compositions can be stored in a freeze-dried (lyophilized) condition, which requires the addition of a sterile liquid carrier, e.g., sterile saline solution for injections, prior to use. Extemporaneous injection solutions and suspensions may be prepared from sterile powders, granules and tablets. Such compositions should comprise a therapeutically effective amount of a TERTC polypeptide and/or other therapeutic agent, together with a suitable amount of carrier so as to provide the form for proper administration to the patient. The formulation should suit the mode of administration.

Systemic administration can also be by transmucosal or transdermal means. For transmucosal or transdermal administration, penetrants appropriate to the barrier to be permeated are used in the formulation. Penetrants for transmucosal administration are generally known in the art, and include, for example, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Pharmaceutical compositions adapted for transdermal administration can be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols, or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable compositions. In these compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for oral administration may be provided, for example, as capsules, tablets, powders, granules, solutions, syrups, suspensions (in aqueous or non-aqueous liquids), edible foams, whips, or emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatin capsules may comprise, for example, vegetable oils, waxes, fats, semi-solid, or liquid polyols. Solutions and syrups may comprise, for example, water, polyols and sugars.

Pharmaceutically compatible binding agents, and/or adjuvant materials can be included as part of the composition. The tablets, pills, capsules, and troches can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location. Oral formulations preferably comprise 10% to 95% active ingredient by weight.

Pharmaceutical compositions adapted for nasal administration can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers such as, for example, nasal sprays or nasal drops. These compositions may comprise aqueous or oil solutions of the active ingredient. Compositions for administration by inhalation may be supplied in specially adapted devices including, but not limited to, pressurized aerosols, nebulizers, or insufflators, which can be constructed so as to provide predetermined dosages of the active ingredient.

Pharmaceutical compositions adapted for rectal administration can be prepared in the form of suppositories (e.g., with conventional suppository bases such as cocoa butter and other glycerides) or retention enemas for rectal delivery. Pharmaceutical compositions adapted for vaginal administration may be provided, for example, as pessaries, tampons, creams, gels, pastes, foams, or spray formulations.

In one embodiment, a pharmaceutical composition of the invention is delivered by a controlled-release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Encl. J. Med. 321:574). In another embodiment, the compound can be delivered in a vesicle, in particular a liposome (See, e.g., Langer, 1990, Science 249:1527-1533; Treat et al., 1989, in *Liposomes in the Therapy of Infectious Disease and Cancer*, Lopez-Berestein and Fidler (eds.) Liss, New York, pp. 353-65; Lopez-Berestein, ibid., pp. 317-27; International Patent Publication No. WO 91/04014; U.S. Pat. No. 4,704, 355). In another embodiment, polymeric materials can be used (See, e.g., *Medical Applications of Controlled Release*, Langer and Wise (eds.) CRC Press: Boca Raton, Fla., 1974; *Controlled Drug Bioavailability Drug Product Design and Performance*, Smolen and Ball (eds.) Wiley: New York (1984); Ranger and Peppas, 1953, J. Macromol. Sci. Rev. Macromol. Chem. 23:61; Levy et al., 1985, Science. 228: 190; During et al., 1989, Ann Neurol. 25:351; Howard et al., 1989, J. Neurosurg. 71:105).

In one embodiment, the active compounds, which comprise polynucleotides, polypeptides, or analogs of the invention, are prepared with carriers that will protect the compound from rapid elimination from the body. Such carriers can be a controlled release formulation, which includes, but is not limited to, implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In a particular embodiment, polypeptides of the invention can be administered using a biodegradable polymer having reverse thermal gelatin properties (See, e.g., U.S. Pat. No. 5,702,717).

In yet another embodiment, a controlled release system can be placed in proximity of the target. For example, a micropump may deliver controlled doses directly into the axillary lymph node region, thereby requiring only a fraction of the systemic dose (See, e.g., Goodson, 1984, in Medical Applications of Controlled Release, vol. 2, pp. 115-138).

In one embodiment, it may be desirable to administer a pharmaceutical composition of the invention locally to the area in need of treatment; this may be achieved, for example, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers. Suppositories generally comprise active ingredients in the range of 0.5% to 10% by weight.

Pharmaceutical compositions suitable for injectable use include sterile aqueous solutions, or dispersions, or sterile powders (for the extemporaneous preparation of sterile injectable solutions or dispersions). For intravenous administration, suitable carriers include physiological saline, bacteriostatic water, Cremophor ELTM (BASF; Parsippany, N.J.) or phosphate buffered saline (PBS). The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, or by the use of a surfactant. Prevention of the action of microorganisms can be achieved by various antibacterial and antifungal agents, such as for example, parabens, chlorobutanol, phenol, ascorbic acid, and thimerosal. It can be preferable to include in the composition isotonic agents, such as for example, sugars, polyalcohols (e.g., mannitol), sorbitol, and sodium chloride. Prolonged absorption of the injectable compositions can be brought about by including in the composition an agent which delays absorption, such as for example, aluminum monostearate and gelatin.

Sterile injectable solutions can be prepared by incorporating the required amount of an active compound (e.g., a polypeptide or antibody) in an appropriate solvent with one or a combination of ingredients enumerated above, as required, followed by filtered sterilization. Generally, dispersions are prepared by incorporating the active compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder comprising the active ingredient.

For administration by inhalation, the compounds are delivered in the form of an aerosol spray from a pressurized container or dispenser which comprises a suitable propellant, e.g., a gas such as carbon dioxide, or a nebulizer.

Oral or parenteral compositions can be formulated in dosage unit form for ease of administration and uniformity of dosage. Dosage unit form as used herein refers to physically discrete units suited as unitary dosages for the subject to be treated, such that each unit contains a predetermined quantity of active compound, which is calculated to produce the desired therapeutic effect, and a pharmaceutical carrier. The skilled artisan will appreciate that dosage unit forms are dependent on the unique characteristics of the active compound, the particular therapeutic effect to be achieved, and the limitations inherent in the art of compounding such an active compound for human administration.

In one embodiment, a therapeutically effective amount of a polypeptide of the invention ranges from about 0.001 to 30 mg/kg body weight. In another embodiment, a therapeutically effective amount of a polypeptide of the invention ranges from about 0.01 to 25 mg/kg body weight. In another embodiment, a therapeutically effective amount of a polypeptide of the invention ranges from about 0.1 to 20 mg/kg body weight. In yet another embodiment, a therapeutically effective amount of a polypeptide of the invention ranges from about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dose necessary to effectively treat a subject, which factors include, but are not limited to, previous treatment regimens, severity of the disease or disorder, general health and/or age of the subject, and concurrent diseases. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

5.6.7 Kits.

The pharmaceutical compositions of the invention can be included in a kit comprising a container, pack, or dispenser together with instructions for administration.

The invention also encompasses kits for detecting the presence of a TERTC polypeptide or polynucleotide of the invention in a biological sample (a test sample) after treatment using TERTC polynulceotides or polypeptides have begun.

In an exemplary embodiment, a kit comprises, in a first container, a purified TERTC nucleic acid or TERTC polypeptide, and in a second container, a molecule that binds to the TERTC nucleic acid or TERTC polypeptide when bound to an analyte in a biological sample.

The kit, for example, can comprise a labeled compound or agent capable of detecting the TERTC polypeptide or TERTC mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide).

For antibody-based kits, the kit can comprise, for example: (1) a first antibody (e.g., attached to a solid support) which binds to a polypeptide of the invention; and, optionally, (2) a second, different antibody which binds to either the TERTC polypeptide or the first antibody and is conjugated to a detectable agent.

For oligonucleotide-based kits, the kit can comprise, for example: (1) an oligonucleotide, e.g., a detectably labeled oligonucleotide, which hybridizes to a TERTC polynucleotide encoding a polypeptide of the invention or (2) a pair of primers useful for amplifying a polynucleotide encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also comprise a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The present invention may be better understood by reference to the following non-limiting examples, which are provided only as exemplary of the invention. The following examples are presented to more fully illustrate the preferred embodiments of the invention. The examples should in no way be construed, however, as limiting the broader scope of the invention.

6. EXAMPLES

In this example, the function of hTERT C-terminus and its potential application in cancer therapy is investigated. In an exemplary TERTC polypeptide, most of the conserved RT-motifs and the hTR-binding domains were deleted (FIG. 1A). The telomerase positive human cervical carcinoma HeLa cells were used. HeLa cells stably expressing the hTERT C27 were generated using a tetracycline controlled (Tet-off) expression system or by infection of cells with a recombinant retroviruses expression system. The data shows that ectopic overexpression of hTERT C27 induced HeLa cells into a senescence-like growth arrest and apoptosis in vitro in cell culture. It also inhibited HeLa cell growth and solid tumor formation in vivo in the xenografted nude mice model. The data also showed that the ectopic expressed hTERT C27 is capable of nuclear translocation and induction of acute chromosome end-to-end fusions, which is the characteristic of telomere dysfunction. This occurs without affecting cellular telomerase enzymatic activity of the transfected cells. Furthermore, it provided strong evidence that the TERT C-terminus fragment alone can induce telomere dysfunction and exhibit anti-proliferation activities and that the C-terminus of hTERT is required for hTERT-mediated maintenance of telomere integrity.

6.1 Materials and Methods 6.1.1 EGFP-hTERTC27 Expression Constructs.

The plasmid pCI-neo-hTERT contains a cDNA encoding the full-length wild-type hTERT. A DNA fragment encoding the 27 KDa hTERT C-terminal polypeptide (the hTERT amino acid 882-1132, termed hTERT C27) was generated by PCR from pCI-neo-hTERT and the sequence was confirmed by DNA sequencing. Two constructs were created expressing the truncated protein with a N-terminal EGFP tag. One construct, pLEGFP-hTERT C27 contains hTERT C27 fragment inserted in-frame into the EcoR I and Sal I sites of the retroviral expression vector pLEGFP-C1 (Clontech). The second construct is a tetracycline-regulated expression plasmid. The fragment encoding EGFP-hTERT C27 was isolated from pLEGFP-hTERT C27 by Nco I (blunt) and Sal I digestions and cloned into the BamH I (blunt) and Sal I sites of the expression vector pRevTRE (Clontech), creating the expression plasmid pTetEGFP-hTERT C27. The expression of EGFP-hTERT C27 is under the control of a tetracycline-regulated promoter. A third construct was created by inserting the hTERT C27 fragment in frame into the BglII site and SalI sites of the retroviral expression vector pEGFP C-1 (Clontech), creating the expression plasmid pLEGFP-hTERTC27. In this construct, the expressed hTERTC27 has an EGFP tag fused at its N-terminus. The expression of this construct was under the control of a minimum CMV promoter.

6.1.2 Generation of Stable Clones of HeLa Cells Expressing EGFP-hTERT C27.

The pLEGFP-hTERT C27 and the control pLEGFPC-1 vectors were transfected into the packaging cell lines PT67 (Clontech) and recombinant retrovirus was prepared and infected HeLa cells according to the procedure described in the "Retroviral gene transfer and expression user manual" (Clontech). After infection, cells were selected in growth medium containing 400 µg/ml G-418 (GIBCO BRL) for 5 days or up to 2 weeks. Cells surviving from G418 selection were either pooled for use or expanded in the same selection medium.

pTetEGFP-hTERT C27 constructs and the control pRevTRE vector were transfected into the HeLa Tet-off cells (Clontech) by calcium phosphate coprecipitation. HeLa Tet-off is a G418-resistant HeLa derived clonal cell line that stably expresses that tetracycline-controlled trans-activator (tRA). HeLa Tet-off cells transfected with pTet EGFP-hTERT C27 were grown in the presence of doxycycline (100 ng/ml) and hygromycin (200 µg/ml). Hygromycin-resistant clones were isolated by ring cloning and tested for expression of hTERT C27 polypeptides after induction by withdrawal of doxycycline from the culture media (doxycycline acts as a repressor of gene expression in this Tet-off system).

6.1.3 Western Blotting for the Detection of hTERT C27 and Fluorescence Microscopy for Visualization of Chromosomal DNA and hTERT C27.

Expression of the hTERT C27 construct was detected by Western blotting using anti-hTERT C-terminal fragment antibodies (Santa Cruz, sc-7212). Cell homogenates were prepared at the indicated time or at different time points after $H_2O_2$ treatment for Western blot analysis. The expressions of the hTERTC27 polypeptide and p21 proteins were detected using specific antibody against EGFP (Clontech, # 8367-1) and p21 (Santa Cruz, sc-6246), respectively.

To determine the subcellular localization of the ectopic expressed polypeptides in living cells, cells were grown on 60 mm cell culture plates and observed directly under a Zeiss Axioplan inverse microscope. To visualize the chromosomal DNA, cells were fixed with methanol and stained with propidium iodide (PI) for observation. Micrographs were recorded with a Kodak DCS200 digital camera. Images were noise-filtered, corrected for background, and merged using Adobe Photoshop. To conduct chromosome analysis in anaphase cells, anaphase cells were visualized by PI staining of cells grown on the coverslip for the indicated time points in the presence or absence of doxycycline.

6.1.4 Cell Growth, Senescence, and Apoptosis.

Cells were plated in duplicate into cell culture plates at the density of $2.0 \times 10^5$ cells/60 mm dish 24 hours before the experiment. Prior to the initiation of an experiment, cells were washed three times with medium containing hygromycin (100 µg/ml) in the presence or absence of doxycycline (100 ng/ml), and treated for various time points as indicated in the text. At the end of experiments, cells were harvested and number of viable cells counted by trypan blue staining.

For cell senescence assays, cells were induced to express hTERT C27 for 7 days and stained for senescence associated β-galactosidase (SA β-galactosidase) by the method of van Steensel et al., (1998) Cell, 92:401-413; and Dimri et al., (1995) Proc. Natl. Acad. Sci. 92:9363-9367. Briefly, cells were washed twice in PBS (pH 7.2), fixed for 5 min in 2% formaldehyde/0.2% glutaraldehyde solution in PBS, washed once in PBS (pH 7.2), and stained with X-gal (1 mg/ml) in 150 mM NaCl, 2 mM $MgCl_2$, 5 mM $K_3Fe(CN)_6$, 5 mM $K_4Fe(CN)_6$, and 40 mM NaPi (pH 6.0) for 12 hr at 37° C.

For quantitative analysis of apoptosis, cells were harvested at indicated time points, washed once in ice-cold PBS, and incubated with annexin V-fluoroescein/PI (Boehringer Mannheim) in calcium-containing HEPES buffer and then immediately analyzed with a FACScan machine (Becton Dickinson).

6.1.5 Telomerase Activity and Telomere Length Assays.

Telomerase activity was determined by a highly sensitive, PCR-based telomere repeat amplification protocol (TRAP)-ELISA assay, using a Telomerase PCR ELISA Kit (Roche) following manufacturer's instructions. Telomere length was analyzed by the terminal restriction fragment length (TRF) assay using a Telo TTAGGG Telomere Length Assay Kit (Roche). Briefly, genomic DNA was isolated from cells. The DNA was analyzed by Southern blots probed with a telomere-specific probe to visualize the TRF.

6.1.6 Nude Mice Xenograft.

Nude mice (age between 5-6 weeks) were used for tumor xenograft assay. The untreated HeLa cells consistently form localized tumors in nude mice approximately 4 weeks after s.c. injection of $2 \times 10^6$ cells. Pooled HeLa cells stably expressing EGFP-hTERT C27 or EGFP were generated by pLEGFP-hTERT or pLEGFP virus-infection followed by G418 selection as mentioned above. Cells were harvested in log-phase growth, washed twice in PBS, resuspended in DMEM medium ($1 \times 10^7$ cells/ml), and injected (0.2 ml) subcutaneously at the base of right flank at $2 \times 10^6$ cells per mouse. Tumor growth was monitored weekly for 4 weeks and tumor size was determined by the product of two perpendicular diameters and the height above the skin surface.

6.1.7 Hydrogen Peroxide Treatment.

Stable transfected cell lines were grown in 100 mm cell culture dishes to 80% confluence. Cells were washed 3 times with DMEM medium and then treated for 2 h with 100 µM $H_2O_2$ diluted in DMEM medium. After the treatment, cells were trypsinized, re-seeded at the density of $1 \times 10^5$ cells/60 mm dish or $1-2 \times 10^4$ cells per well in 24-well plates as indicated, and cultured for 7 to 9 days. Growth medium were changed at day 3 after the treatment.

6.2 Results 6.2.1 hTERT C27 Polypeptide and the Effect on Endogenous TERT Level

As an example of a C-terminus hTERT polypeptide, a truncated hTERT (residues 882-1132) with the N-terminus 881 amino acids deleted was constructed. The deleted region includes all of the TR binding domain and most of the conserved RT-domains. This truncated version. (hTERT C27) encodes a 27 KDa polypeptide of the hTERT C-terminal fragment, with its N-terminus fused with EGFP so that its expression and cellular localization can be traced in living cells.

To achieve regulated expression of this fusion protein, we generated a construct pTetEGFP-hTERT C27, and the expression of this construct was under the control of a tetracycline-regulated promoter. The pTetEGFP-hTERT C27 plasmid was transfected into human cervical carcinoma HeLa Tet-off cell line, and clones of cells stably expressing EGFP-hTERT C27 were isolated by the hygromycine selection. Among 56 such clones, two clones (C8 and G11), upon the withdrawal of doxycyclin, showed high level of expression of EGFP-hTERT C27 (with the predictive size of 54 kDa). These two clones were therefore selected for use as examples. Only the data from clone C8 is presented, as similar results were also obtained from clone G11. A representative Western blotting data of clone C8 is shown in FIG. 1B. The result shows that the induction of the EGFP hTERT C27 expression by doxycyclin withdrawal had no effect on the expression level of endogenous full-length hTERT protein.

6.2.2 Ectopic Over-Expression of C27 Leads to Senescence-Like Growth Arrest and Apoptosis.

Figure 2:
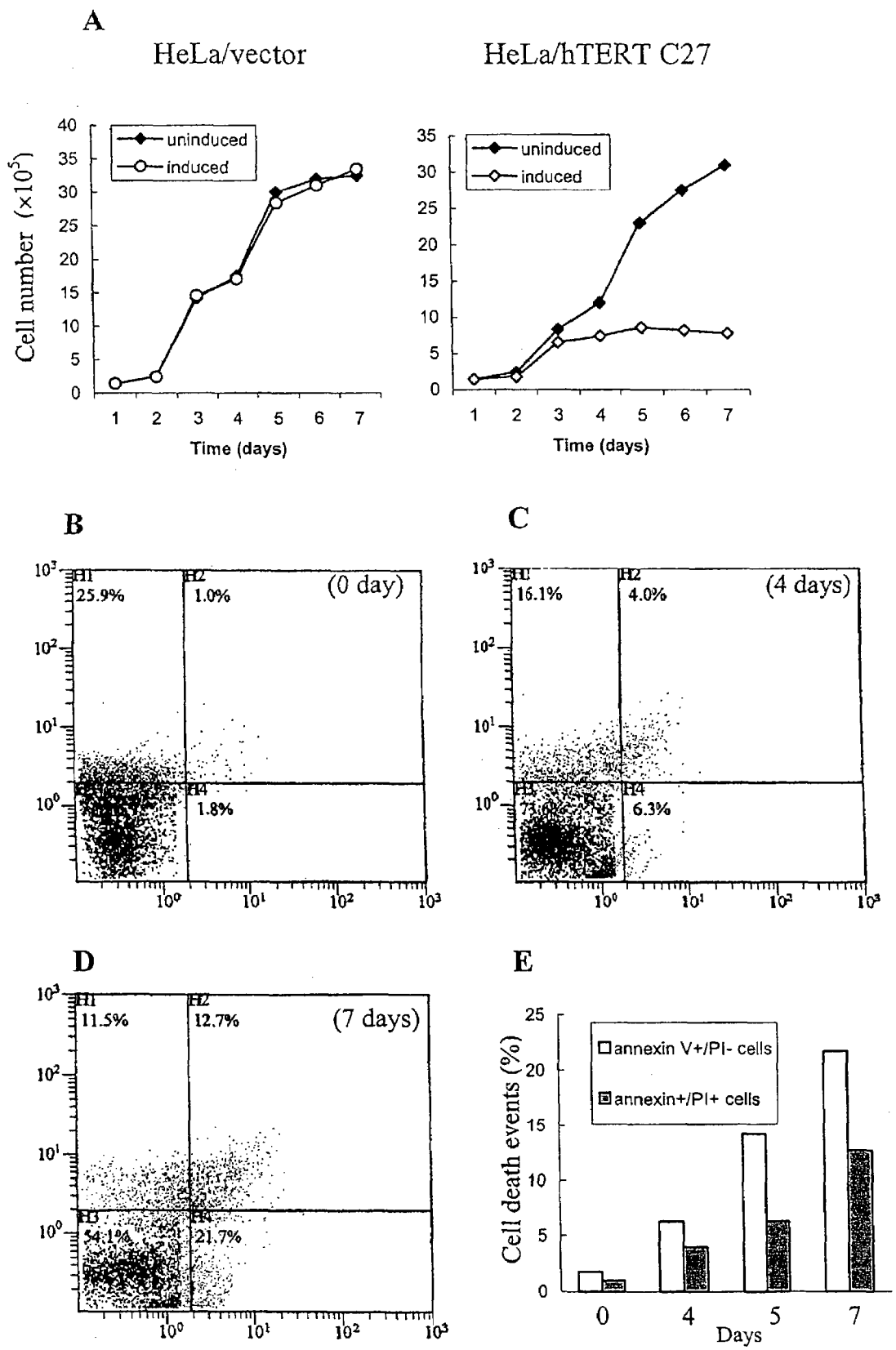

The effect of hTERT C27 expression on cell proliferation was first analyzed using the isolated inducible transfectant HeLa Tet-off clone C8. Induction of C27 expression in this clone caused a time dependent inhibition of the rate of cell proliferation (FIG. 2A). Significant inhibition was noticed from day 3 days onward after the induction of C27 expression. Cell growth was nearly completely inhibited at 7 days after doxycyclin withdrawal from the culture medium.

Using the trypan blue exclusion assay, it was found that induction of C27 expression caused a noticeable increase of non-viable cells (from approximately 5% of the total cells in the non C27 expressing cells, to 25% in the C27 expressing cells after 4 days). To determine if this is due to apoptosis, the percentage of apoptotic cells was measured using flow-cytometry analysis of cells double labeled with annexin V and propidium iodide (PI). The annexin V binding property is a marker for early apoptotic cells (Vermes et al., 1995. J. Immunol. Meth., 184:39-51), while PI staining reflects the late stage of cell death. Therefore, annexin V and PI double labeling allows a further distinction of early apoptotic (annexin V+/PI−, shown in FIG. 2B-D as the H4 section) and late apoptotic/necrotic (V+/PI+, shown in FIG. 2B-D as the H2 section) cells. In a typical experiment, prior to the induction of EGFP-hTERT C27 expression, basal apoptosis was low (FIG. 2B, 1.8% annexin V+/PI−, H4 section, and 1.0% annexin V+/PI+, H2 section). From day 4 to day 7, there is a time dependent increase in percentage of apoptotic cells both in early and late phase. At day 4 (FIGS. 2C and 2E), a significant increase of both early and late apoptotic cells (6.3% annexin V+/PI− and 4.0% annexin V+/PI+cells) were detected in C27 expressing HeLa cells, while no increase was found in the non-induced cells. At day 5, 14.2 and 6.3% of cells were in the early and late apoptosis state, respectively (FIG. 2E). At day 7, massive apoptosis was observed (FIGS. 2D and 2E, 21.7% annexin V+/PI− cells and 12.7% annexin V+/PI+ cells). The percentage of apoptotic cells remained at approximately 3-5% of the total cells in control non-induced cells over the time under the same experimental conditions.

Figure 3:
Figure 3:
Figure 3:
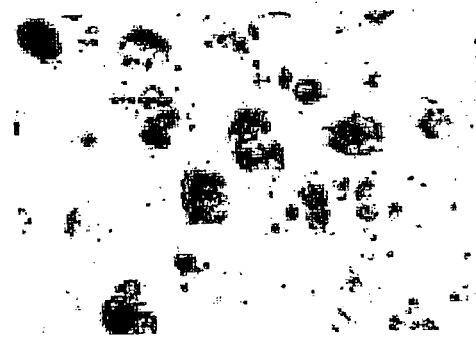
Figure 3:

In addition, expression of C27 also caused marked changes in cell morphology (FIG. 3A-D). At day 4 post-induction, while the control non-induced cells exhibited normal morphology (FIG. 3A), a noticeable number of the C27 expressing cells became enlarged and flattened with a vacuolated cytoplasm. Most of these enlarged cells showed positive staining of senescence-associated B-galactosidase (SA 1-gel) (FIG. 3B), a phenotype reminiscent to that of the primary human cells undergoing senescence (44). The percentage of cells that became senescence-like continues to increase, and at the 7th day post-induction, most of the cells became senescent (FIG. 3C). Consistent with the cellular senescence phenotype, this cell growth arrest was irreversible, as replenishing the media with doxycycline to suppress C27 expression on day 6 post-induction for 7 days could not reverse the changes in cell morphology or the rate of cell proliferation. These cells remain enlarged and flattened (FIG. 3D). Therefore, the results showed that overexpression of C27 inhibited HeLa cell proliferation by inducing both cell senescence and apoptosis.

6.2.3 hTERT C27 Causes Chromosome End-To-End Fusions.

Figure 4:
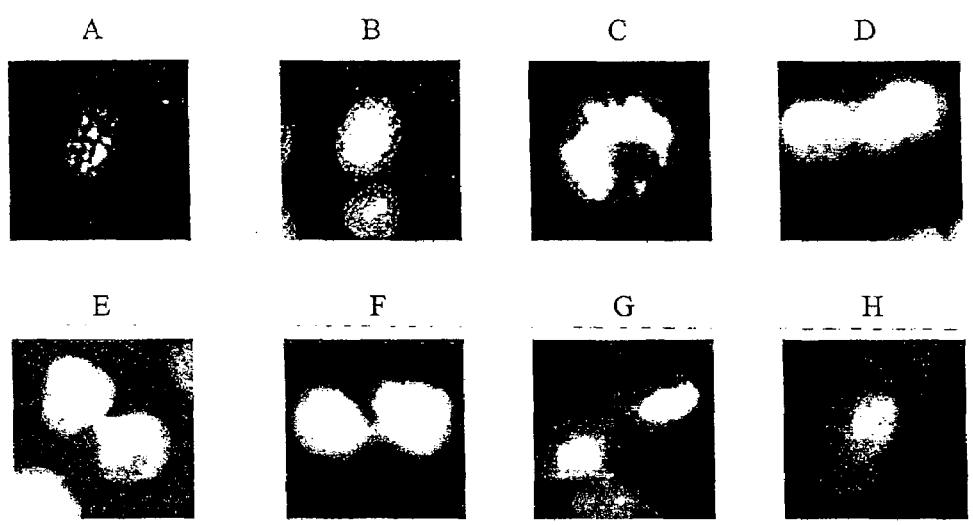

The most important biological function of telomerase and hTERT on cancer cell immortalization is to maintain the integrity of the telomere structure at the chromosome ends. Therefore, whether and how C27 expression affected telomere structure was examined. Cells were induced to express EGFP-hTERT C27 for indicated time and then fixed by methanol for analysis of aberrant chromosome events. The subcellular localization of C27 was examined under fluorescent microscope following the green fluorescent signal provided by EGFP tracer. It was showed that the hTERT-C27 alone contains sufficient signal for its nuclear localization. After the induction of EGFP-hTERT C27 expression, the fusion protein accumulated in the nucleus, as all green fluorescence signals were clearly seen in the nucleus with a punctate localization pattern, while no signal could be detected in the cytosol (FIG. 4A, green color for EGFP). When the chromosomal DNA was stained with PI, the expressed C27 fusion proteins were found to be localized on both the interphase (FIG. 4B) and the mitotic chromosomes (FIG. 4C). At 4 days post-induction, significantly increased chromosome end-to-end fusion events were observed in C27 expressing cells (Table 1), which is exemplified with increased anaphase bridges (FIG. 4C) and lagging chromosomes (FIG. 4D-G).

This special nuclear localization pattern was endowed by the C27 polypeptide only, as control wild type EGFP proteins were found only in the cytoplasm. A modified version of C27 was also prepared by adding a HA tag to the C-terminal of the EGFP-hTERT C27 (EGFP-hTERT C27-HA). HeLa cells were then transiently transfected with this EGFP-hTERT-C27 HA plasmid. The modified fusion protein showed diffused nuclear expression pattern with a small fraction of the protein expressed in the cytosol. There was no punctate localization pattern, indicating that it is not located at a particular point of the chromosome (FIG. 4H). Therefore, addition of the HA tag at the C-terminus of C27 appears to decrease its ability for proper nuclear translocation and abolish its binding to the chromosome end. This indicates that the C-terminus, particularly an unhindered C-terminus, is essential for the nuclear translocation and binding to the chromosome ends. Modification of the C-terminus therefore, may result in the loss of these functions.

Results from the cytogenetic analysis were combined and presented in Table 1. The expression of C27 caused a significant increase in the occurrence of aberrant chromosomes, including anaphase bridges and lagging chromosomes, evident for a chromosome end-to-end fusion. In the cells transfected with control EGFP vector, no change in the frequency of chromosomal alteration was observed. Taken together, these results strongly suggest that the binding of C27 to the chromosome, presumably at the telomeres, leads to telomere dysfunction, which is one of the major causes triggering subsequent activation of cellular senescence and apoptotic pathways.

TABLE 1

Induction of anaphase chromosome end to end fusions by C27.

| Cell Line | Induction | No. of cells examined | Fraction with fusion event[a] (%) |
|---|---|---|---|
| HeLa Tet-off | − | 50 | 12 |
| HeLa Tet-off | + | 50 | 12 |
| HeLa-hTERT C27 | − | 100 | 18 |
| HeLa-hTERT C27 | + | 100 | 35 |

[a]Percentage of cells that exhibit chromosome end fusions were determined by calculating the ratio of aberrant mitosis events showing either chromosome bridges or lagging chromosomes to the total mitosis events observed at day 4 post induction.

6.2.4 hTERT C27 Did Not Affect Telomerase Activity.

The phenomenon of telomere dysfunction and cell growth inhibition may be explained if C27 acts in a dominant negative manner to inhibit telomerase activity and hence resulting in telomere shortening. To address this possibility, the effect of C27 expression was analyzed on cellular telomerase activity by the TRAP-ELISA assay. Our result showed that induction of C27 expression had no effect on cellular telomerase activity over time (FIG. 5A). To further support this findings, genomic DNA from C27 expressing HeLa cells was isolated, and the telomere length was determined by terminal restriction fragments (TRF) assay. Again, events of telomere shortening were not observed over time (FIG. 5B). These data confirmed that the cell growth inhibition induced by C27 overexpression was not caused by inhibition of telomerase activity.

6.2.5 Expression of C27 Reduced the Tumorgenicity of the Hela Cells.

Figure 6:
Figure 6:

To evaluate the potential anti-proliferation effect of hTERT C27 in vivo, pooled clones of HeLa cells stably expressing either the EGFP-hTERT C27 or the control EGFP were generated by retrovirus transfection as described in experimental procedure. These cells were then xenografted into nude mice (n=4 per group) and the solid tumor formation and tumor growth were analyzed. As shown in FIG. 6, at four weeks post xenografting, only one of the 4 mice receiving EGFP-hTERT C27 expressing Hela cells developed tumors. The tumor mass was first noticed at day 17 with a slow growth rate and small size of tumor mass at the end of the experiment (FIG. 6A, Table 2). In contrast, all of the 4 mice xenografted with the control EGFP expressing HeLa cells had noticeable tumors appeared on the injected sites before day 13 post xenografting. The tumors grew rapidly and large tumor masses were observed at the end of the experiments (FIG. 6B, Table 2). These results are consistent with the in vitro cell culture study and indicate that hTERT C27 over-expression resulted in a reduced tumorgenicity of the cultured HeLa cells in the mouse xenograft model.

TABLE 2

Prevention of tumor formation in nude mice by the expression of C27.

| Cell line[a] | Incidence of tumor formed[b] | Mean tumor size at 4 weeks (mm$^3$) |
|---|---|---|
| HeLa EGFP | 4/4 | 1298 ± 560 |
| HeLa EGFP | 4/4 | 1304 ± 870 |
| HeLa EGFP-hTERT C27 | 1/4 | 135 |
| HeLa EGFP-hTERT C27 | 1/4 | 109 |

[a]Nude mice were injected s.c. with 2 × 10$^6$ cells of the indicated cell line, and tumors were measured 4 weeks later.
[b]Incidence of tumor formed at 4 weeks after xenograft. Data represent the number of mice with tumor / total number of mice in two separate experiments each with four mice per group.

6.2.6 Hydrogen Peroxide Caused Cell Senescence in hTERT C27 HeLa Cells

High EGFP-hTERTC27 expressing cells, as determined by the intensity of the fluorescence signals, were occasionally found at the early stage of the recombinant retrovirus infection. However, these cells quickly detached from the culture plates and floated in the media during the early stages of G418 selection. This suggests that over-expression of hTERTC27 at high level is deleterious to HeLa cells.

Two stable cell lines, one expressing EGFP-hTERTC27 (C3) and one expressing the control EGFP (A1), were chosen to examine the effect of hTERTC27 on the proliferation of HeLa cells. Western blotting analysis using the EGFP antibody confirmed that low level of EGFP-hTERTC27 (Mr 54,000) was expressed in the two stable clones, but not in the parental non-transfected HeLa cells and the control EGFP transfected cells. As shown in FIG. 7A, C3 cells that express low levels of hTERTC27 exhibited similar growth rate as determined by measuring the number of viable cells by trypan blue method over a 7-day culture, as compared to the A1 cells over expression EGFP (FIG. 7A) and the parental HeLa cells. Similar results were obtained in two additional clones and a pooled clones (12 clones) stablizing expressing the EGFP-hTERTC27 and EGFP, suggesting that a low level of hTERTC27 expression did not change cell proliferation rate.

To test if the C-terminus of hTERT plays a role in cell response to oxidative stress, we examined the effects of hTERTC27 expression on the cellular response to $H_2O_2$-induced cell senescence. The C3 clone stably expressing hTERTC27 and the A1 clone stably expressing EGFP were both treated with a bolus dose of 100 μM hydrogen peroxide (H2O2) for 2 hours. After treatment, the growth of C3 and A1 cells were monitored for 7 days by measuring the number of viable cells by trypan blue method and by examining the cell morphology. The expression of hTERTC27 significantly suppressed cell growth (FIG. 7B, C3 cells) as compared to that of the control A1 cells under the same treatment conditions (FIG. 7B, A1 cells). The C3 cells exhibit strikingly different morphology as visualized under the phase contrast microscope; the cells became enlarged and flattened and lose cell to cell contact but still remained adherent to the culture plate 7 days after the initiation of the $H_2O_2$ treatment. In contrast, the A1 cells under the same $H_2O_2$ treatment exhibited a normal cell morphology like that of the control untreated cells. In addition, $H_2O_2$ treated C3 cells stained positively for SA β-gal, a hallmark for cellular senescence (Chen et al., 2001, Exp. Cell. Res. 265, 294-303), while no SAβ-gal staining was found in the control A1 cells under the same treatment conditions, or the C3 cells without $H_2O_2$ treatment. These results suggest that low level of hTERTC27 expression rendered cells susceptible to $H_2O_2$-induced cell senescence but did not affected rate of cell proliferation.

6.2.7 Hydrogen Peroxide Caused Up-Regulation of $p21^{Waf1}$

The cyclin/cdk inhibitor $p21^{Waf1}$ gene exerts an inhibitory effect on cyclin-dependent kinases and mediates cell growth arrest. Up-regulation of p21 gene expression occurs during the processes of physiologically induced or premature cell senescence (Chen et al., (2001) Exp. Cell. Res. 265, 294-303; Saretzki et al., (1999) Oncogene 18, 5148-5158; Goodwin et al., (2000) Proc. Natl. Acad. Sci. USA 97, 10978-10983; Wells et al., (2000) EMBO J. 19, 5762-5771). The expression of $p21^{Waf1}$ can be regulated through both the p53-dependent and the p53-independent pathway (Damm et al., (2001) EMBO J. 20, 6958-6968). To identify the mechanism for the increased susceptibility to $H_2O_2$ by hTERTC27, $p21^{Waf1}$ protein level was determined. Western blot analysis showed that $p21^{Waf1}$ protein level increased rapidly in $H_2O_2$ treated C3 cells. This up-regulation was maintained for at least 9 days. In contrast, $p21^{Waf1}$ up-regulation was not detected in the control A1 cells under the same treatment conditions. To determine if p53 participated in the up-regulation of p21, the cellular p53 level was examined. In HeLa cells, the wild type p53 protein is expressed but rapidly sequestered by the HPV/E6 viral proteins and degraded. While a control p53 positive human gastric cancer AGS cells showed strong p53 expression, it was not possible to detect p53 proteins in either the C3 or the control A1 cells before or after $H_2O_2$ treatment. These results suggest that $H_2O_2$ induced up-regulation of $p21^{Waf1}$ in C3 cells is mediated through a p53-independent pathway.

6.2.8 Telomerase Activity is Not Affected During Hydrogen Peroxide-Induced Senescence If hTERTC27 acts as a dominant negative form of hTERT, then hTERTC27-induced susceptibility to $H_2O_2$ could be simply due to the inhibition of telomerase activity. To exclude this possibility, we determined the effect of hTERTC27 expression on cellular telomerase activity by the TRAP-ELISA assay. Pooled stable hTERTC27 expressing and EGFP expressing clones of HeLa cells were each exposed to a bolus dose of 100 μM $H_2O_2$ for 2 h and cellular telomerase activity was measured. No change in the cellular telomerase activity was found during the 7-days course after $H_2O_2$ treatment in either the hTERTC27 expressing or the control EGFP clones.

In addition, we isolated genomic DNA from these cells and determined the bulk telomere lengths by terminal restriction fragment (TRF) assay. Our results indicated that the bulk telomere length was not significantly changed in hTERTC27 expressing HeLa cells or the control EGFP expressing cells during the 9-days course after a bolus dose of 100 μM $H_2O_2$ treatment. Therefore, we concluded that the increased sensitivity to $H_2O_2$-induced cells senescence was not due to the inhibition of telomerase enzyme activity or telomere shortening.

6.3 Discussion

Ectopic overexpression of a TERT C-terminal polypeptide in the telomerase positive HeLa cells induced a rapid senescence-like growth arrest and apoptosis. HeLa cells stably expressing the hTERT C27 also exhibited reduced tumorgenicity in the nude mice xenograft model.

All these tumor-suppressing properties are caused by TERTC polypeptide induced telomere dysfunction, as evident by the nuclear and chromosomal localization of the hTERT C27 polypeptide, and the subsequent chromosome end-to-end fusions, which precedes cell growth arrest events. This mechanism is different from all of the previously reported TERT antisense or dominant negative mutants. Previously reported hTERT mutants all resulted in telomere dysfunction by inhibition of telomerase activity, thus causing progressive shortening of the telomere lengths and damage to the telomere structure. In contrast, C27 does not inhibit telomerase activity, and because there is no reduction in telomerase activity, therefore, reducing the possibility of the involvement of the alternating lengthening. Thus, TERT polypeptides and analogs represent a new strategy for cancer treatment, which may provide a more favorable clinical outcome.

The molecular mechanism of TERTC polypeptide induced telomere dysfunction is not known. It is possible that C27 simply acts as an inactive form of hTERT that can translocate by itself to the nucleus and assembles into telomerase ribonucleoprotein (RNP) which could titrate telomerase RNA away from interaction with the endogenous full length catalytically active hTERT. By this model, it is predicted that hTERT C27 should inhibit the endogenous telomerase enzymatic activity and thus the telomere elongation and telomere maintenance. The data showed that this model can be ruled out because there is no change on cellular telomerase activity with ectopic expression of C27.

The phenotypes induced by C27 resemble that of a dominant negative mutant of the telomere binding protein TRF2 (DN-TRF2). Recent evidence has shown that DN-TRF2 acts by interrupting TRF2 binding to telomere which rapidly induces telomere dysfunction and growth inhibition without affecting the enzymatic activity of the telomerase (Van Stensel et al., Cell 92:401-413.) Thus, the data suggests that hTERT C-terminus is responsible for the binding of a component of the telomere complex, possibly TRF2, and this binding allows for precise homing of hTERT to the telomere cap at the chromosome end. It is also possible that other components of the telomere binding proteins such as pot 1 or the human counter part of the yeast Est1/Cdc13 is the target of hTERT C27. In this model, the data show that hTERT has an additional function, i.e., in addition to telomerase enzymatic activity, hTERT plays an important role in protecting the telomere from dysfunction via its C-terminus. As the exogenously expressed C27 is capable of finding its way to the nucleus via 14-3-3, and then to the telomere possibly either via TRF2 or other telomere binding proteins, it can disrupt the proper function of the endogenous full-length hTERT and cause telomere dysfunction.

It is well documented that the normal somatic cells have long telomere, and their telomere lengths shorten with each cell division. When the telomere lengths are shortened to approximately 5-8 kb, cell would enter senescence or crisis. In contrast, the telomere lengths in most telomerase-positive human cancer cells are usually below the range of 5-7 kb or even shorter. It is at present not known why or how cancer cells can survive with such a short telomere without inevitably result in telomere dysfunction, cellular senescence or crisis. Accumulated evidence has also demonstrated that when telomerase are activated by hTERT expression in human diploid cells transformed with an activated oncogene, these cells can endure further telomere shortening without encountering cell senescence or cell crisis. This also suggests that activation of hTERT gene expression and the telomerase activity can stabilize the short telomere structure and prevent telomere dysfunction that is critical for cancer cell immortalization. In view of the critical role of hTERT in the survival of cancer cells, as well as the findings presented hereinabove that a TERTC polypeptide, C27, can induce telomere dysfunction and cell senescence on its own, the clinical application of TERTC polynucleotides, polypeptides and analogs in cancer therapy.

The data also showed that a low level of hTERTC27 expression had no effect on the rate of HeLa cells proliferation but rendered HeLa cells susceptible to a mild dose of hydrogen peroxide which leads to cellular senescence. The data indicate that hTERTC27 renders the TERT positive HeLa cells sensitive to hydrogen peroxide induced cellular senescence through a p21$^{Waf1}$ dependent and p53-independent pathway. The inventors believe that the C-terminus of hTERT has an important function in hTERT-mediated cellular resistance to oxidative stress. In particular, hTERTC27 is believed to disrupt the interaction between the C-terminus of hTERT and the components of either the telomere binding proteins or the DNA damage response machinery Ku, ATM, RAD50, MRE11 and NBS1 located on human telomeres (Wong et al., (2000) Nat. Genet. 26, 85-88; Blackburn, E. H. (2001) Cell 106, 661-673; Peterson et al., (2001) Nat. Genet. 27, 64-67; Samper et al., (2000) EMBO Reports 1, 244-252; Lim et al.,(2000) Nature 404, 613-617; and Zhu et al., (2000) Nat. Genet. 25, 347-352.). This may destabilize the capped telomere structure, which in turn lowered the threshold of the DNA damage response, and rendered cells more sensitive to oxidative stress. The inventors also believe that hTERTC27 can regulate stress response directly via the cellular signaling pathways through 14-3-3, as 14-3-3 is an important family of adaptor proteins that establish interactions among various signaling proteins, therefore, plays critical roles in many cellular physiologic and damage responding processes (Fu et al., (2000) Ann. Rev. Pharmacol. Toxicol. 40, 617-647). By binding to 14-3-3, hTERTC27 could directly modulate cellular signaling pathways.

7. INCORPORATION BY REFERENCE

All publications, patents and patent applications mentioned in this specification are herein incorporated by reference into the specification to the same extent as if each individual publication, patent or patent application was specifically and individually indicated to be incorporated herein by reference.

8. EQUIVALENTS

Having herein above disclosed exemplary embodiments of the present invention, those skilled in the art will recognize that this disclosure is only exemplary such that various alternatives, adaptations, and modifications are within the scope of the invention. Those skilled in the art, through routine experimentation, will be able to ascertain many equivalents to the particular embodiments of the invention described herein. The claimed invention intends to encompass all such equivalents. Accordingly, the present invention is not limited to the specific embodiments as illustrated above, but is defined by the following claims.

What is claimed is:

1. An isolated polynucleotide consisting of a nucleotide sequence that encodes a polypeptide consisting of the entire polypetide SEQ ID NO: 2.

2. A vector comprising the polynucleotide of claim 1.

3. The vetor of claim 2 further comprising a regulatory sequence operably linked to the polnucleotide.

4. The vector of claim 3, wherein the regulatory sequence comprises an inducible promoter, cell-specific promoter, or disease-specific promoter.

5. A composition comprising the vecter of any one of claims 2, 3, or 4, and a pharmaceutically acceptable carrier.

6. An isolated cell comprising the vector of any one of claims 2, 3, or 4.

7. A method for preparing the polypeptide of SEQ ID NO:2, comprising (i) culturing the cell of claim 6 under conditions such that the polypeptide is produced by the cell, and (ii) recovering the polypeptide. under conditions such that the polypeptide is made in the cell, and (ii) recovering the polypeptide.

* * * * *

SEQUENCE LISTING

```
<160> NUMBER OF SEQ ID NOS: 2

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (2702)..(3454)

<400> SEQUENCE: 1
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
```

-continued

```
gccgctggcc acgttcgtgc ggcgcctggg gccccagggc tggcggctgg tgcagcgcgg      180
ggacccggcg gctttccgcg cgctggtggc ccagtgcctg gtgtgcgtgc cctgggacgc      240
acggccgccc ccgccgccc cctccttccg ccaggtgtcc tgcctgaagg agctggtggc      300
ccgagtgctg cagaggctgt gcgagcgcgg cgcgaagaac gtgctggcct tcggcttcgc      360
gctgctggac ggggcccgcg ggggccccc cgaggccttc accaccagcg tgcgcagcta      420
cctgcccaac acggtgaccg acgcactgcg ggggagcggg gcgtggggc tgctgctgcg      480 ccgcgtgggc gacgacgtgc tggttcacct gctggcacgc tgcgcgctct ttgtgctggt      540
ggctcccagc tgcgcctacc aggtgtgcgg gccgccgctg taccagctcg cgctgccac      600 tcaggcccgg cccccgccac acgctagtgg accccgaagg cgtctgggat gcgaacgggc      660
ctggaaccat agcgtcaggg aggccggggt ccccctgggc ctgccagccc cgggtgcgag      720
gaggcgcggg ggcagtgcca gccgaagtct gccgttgccc aagaggccca ggcgtggcgc      780 tgccctgag ccggagcgga cgccgttgg gcagggtcc tgggcccacc cgggcaggac      840
gcgtggaccg agtgaccgtg gtttctgtgt ggtgtcacct gccagacccg ccgaagaagc      900
cacctctttg gagggtgcgc tctctggcac gcgccactcc cacccatccg tgggccgcca      960
gcaccacgcg ggcccccat ccacatcgcg gccaccacgt ccctgggaca cgccttgtcc     1020
cccggtgtac gccgagacca agcacttcct ctactcctca ggcgacaagg agcagctgcg     1080
gccctccttc ctactcagct ctctgaggcc cagcctgact ggcgctcgga ggctcgtgga     1140
gaccatcttt ctgggttcca ggccctggat gccaggact ccccgcaggt tgccccgcct     1200
gccccagcgc tactggcaaa tgcggcccct gtttctggag ctgcttggga accacgcgca     1260
gtgcccctac ggggtgctcc tcaagacgca ctgcccgctg cgagctgcgg tcaccccagc     1320
agccggtgtc tgtgcccggg agaagcccca gggctctgtg gcggccccg aggaggagga     1380 cacagacccc cgtcgcctgg tgcagctgct ccgccagcac agcagcccct ggcaggtgta     1440
cggcttcgtg cgggcctgcc tgcgccggct ggtgccccca ggcctctggg gctccaggca     1500
caacgaacgc cgcttcctca ggaacaccaa gaagttcatc tccctgggga agcatgccaa     1560
gctctcgctg caggagctga cgtggaagat gagcgtgcgg gactgcgctt ggctgcgcag     1620
gagcccaggg gttggctgtg ttccggccgc agagcaccgt ctgcgtgagg agatcctggc     1680
caagttcctg cactggctga tgagtgtgta cgtcgtcgag ctgctcaggt ctttctttta     1740
tgtcacggag accacgtttc aaaagaacag gctcttttc taccggaaga gtgtctggag     1800
caagttgcaa agcattggaa tcagacagca cttgaagagg gtgcagctgc gggagctgtc     1860
ggaagcagag gtcaggcagc atcgggaagc caggcccgcc ctgctgacgt ccagactccg     1920
cttcatcccc aagcctgacg ggctgcggcc gattgtgaac atggactacg tcgtgggagc     1980
cagaacgttc cgcagagaaa agagggccga gcgtctcacc tcgagggtga aggcactgtt     2040
cagcgtgctc aactacgagc gggcgcgcg ccccggcctc ctgggcgcct ctgtgctggg     2100
cctggacgat atccacaggg cctggcgcac cttcgtgctg cgtgtgcggg cccaggaccc     2160
gccgcctgag ctgtactttg tcaaggtgga tgtgacgggc gcgtacgaca ccatccccca     2220
ggacaggctc acggaggtca tcgccagcat catcaaaccc cagaacacgt actgcgtgcg     2280
tcggtatgcc gtggtccaga aggccgccca tgggcacgtc gcaaggcct tcaagagcca     2340 cgtctctacc ttgacagacc tccagccgta catgcgacag ttcgtggctc acctgcagga     2400
gaccagcccg ctgagggatg ccgtcgtcat cgagcagagc tcctccctga atgaggccag     2460
cagtggcctc ttcgacgtct tcctacgctt catgtgccac cacgccgtgc gcatcagggg     2520
```

```
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct cacctcaccc acgcgaaaac    2700
```

```
c ttc ctc agg acc ctg gtc cga ggt gtc cct gag tat ggc tgc gtg gtg       2749
  Phe Leu Arg Thr Leu Val Arg Gly Val Pro Glu Tyr Gly Cys Val Val
  1               5                   10                  15 aac ttg cgg aag aca gtg gtg aac ttc cct gta gaa gac gag gcc ctg         2797
Asn Leu Arg Lys Thr Val Val Asn Phe Pro Val Glu Asp Glu Ala Leu
                20                  25                  30 ggt ggc acg gct ttt gtt cag atg ccg gcc cac ggc cta ttc ccc tgg         2845
Gly Gly Thr Ala Phe Val Gln Met Pro Ala His Gly Leu Phe Pro Trp
            35                  40                  45 tgc ggc ctg ctg ctg gat acc cgg acc ctg gag gtg cag agc gac tac         2893
Cys Gly Leu Leu Leu Asp Thr Arg Thr Leu Glu Val Gln Ser Asp Tyr
50                  55                  60 tcc agc tat gcc cgg acc tcc atc aga gcc agt ctc acc ttc aac cgc         2941
Ser Ser Tyr Ala Arg Thr Ser Ile Arg Ala Ser Leu Thr Phe Asn Arg
65                  70                  75                  80 ggc ttc aag gct ggg agg aac atg cgt cgc aaa ctc ttt ggg gtc ttg         2989
Gly Phe Lys Ala Gly Arg Asn Met Arg Arg Lys Leu Phe Gly Val Leu
                85                  90                  95 cgg ctg aag tgt cac agc ctg ttt ctg gat ttg cag gtg aac agc ctc         3037
Arg Leu Lys Cys His Ser Leu Phe Leu Asp Leu Gln Val Asn Ser Leu
                100                 105                 110 cag acg gtg tgc acc aac atc tac aag atc ctc ctg ctg cag gcg tac         3085
Gln Thr Val Cys Thr Asn Ile Tyr Lys Ile Leu Leu Leu Gln Ala Tyr
            115                 120                 125 agg ttt cac gca tgt gtg ctg cag ctc cca ttt cat cag caa gtt tgg         3133
Arg Phe His Ala Cys Val Leu Gln Leu Pro Phe His Gln Gln Val Trp
        130                 135                 140 aag aac ccc aca ttt ttc ctg cgc gtc atc tct gac acg gcc tcc ctc         3181
Lys Asn Pro Thr Phe Phe Leu Arg Val Ile Ser Asp Thr Ala Ser Leu
145                 150                 155                 160 tgc tac tcc atc ctg aaa gcc aag aac gca ggg atg tcg ctg ggg gcc         3229
Cys Tyr Ser Ile Leu Lys Ala Lys Asn Ala Gly Met Ser Leu Gly Ala
                165                 170                 175 aag ggc gcc gcc ggc cct ctg ccc tcc gag gcc gtg cag tgg ctg tgc         3277
Lys Gly Ala Ala Gly Pro Leu Pro Ser Glu Ala Val Gln Trp Leu Cys
            180                 185                 190 cac caa gca ttc ctg ctc aag ctg act cga cac cgt gtc acc tac gtg         3325
His Gln Ala Phe Leu Leu Lys Leu Thr Arg His Arg Val Thr Tyr Val
        195                 200                 205 cca ctc ctg ggg tca ctc agg aca gcc cag acg cag ctg agt cgg aag         3373
Pro Leu Leu Gly Ser Leu Arg Thr Ala Gln Thr Gln Leu Ser Arg Lys
    210                 215                 220 ctc ccg ggg acg acg ctg act gcc ctg gag gcc gca gcc aac ccg gca         3421
Leu Pro Gly Thr Thr Leu Thr Ala Leu Glu Ala Ala Ala Asn Pro Ala
225                 230                 235                 240 ctg ccc tca gac ttc aag acc atc ctg gac tga tggccacccg cccacagcca      3474
Leu Pro Ser Asp Phe Lys Thr Ile Leu Asp
                245                 250
```

```
ggccgagagc agacaccagc agccctgtca cgccgggctc tacgtcccag ggagggaggg    3534
gcggcccaca cccaggcccg caccgctggg agtctgaggc ctgagtgagt gtttggccga    3594
ggcctgcatg tccggctgaa ggctgagtgt ccggctgagg cctgagcgag tgtccagcca    3654
agggctgagt gtccagcaca cctgccgtct tcacttcccc acaggctggc gctcggctcc    3714
```

```
accccagggc cagcttttcc tcaccaggag cccggcttcc actccccaca taggaatagt    3774
ccatccccag attcgccatt gttcacccct cgccctgccc tcctttgcct tccacccca    3834 ccatccaggt ggagaccctg agaaggaccc tgggagctct gggaatttgg agtgaccaaa    3894
ggtgtgccct gtacacaggc gaggaccctg cacctggatg ggggtccctg tgggtcaaat    3954 tgggggagg tgctgtggga gtaaaatact gaatatatga gttttcagt tttgaaaaaa    4014 a                                                                    4015
```

<210> SEQ ID NO 2
<211> LENGTH: 250
<212> TYPE: PRT
<213> ORGANISM: Homo sapiens

<400> SEQUENCE: 2

```
Phe Leu Arg Thr Leu Val Arg Gly Val Pro Glu Tyr Gly Cys Val Val
1               5                   10                  15

Asn Leu Arg Lys Thr Val Val Asn Phe Pro Val Glu Asp Glu Ala Leu
            20                  25                  30

Gly Gly Thr Ala Phe Val Gln Met Pro Ala His Gly Leu Phe Pro Trp
        35                  40                  45

Cys Gly Leu Leu Leu Asp Thr Arg Thr Leu Glu Val Gln Ser Asp Tyr
    50                  55                  60

Ser Ser Tyr Ala Arg Thr Ser Ile Arg Ala Ser Leu Thr Phe Asn Arg
65                  70                  75                  80

Gly Phe Lys Ala Gly Arg Asn Met Arg Arg Lys Leu Phe Gly Val Leu
                85                  90                  95

Arg Leu Lys Cys His Ser Leu Phe Leu Asp Leu Gln Val Asn Ser Leu
            100                 105                 110

Gln Thr Val Cys Thr Asn Ile Tyr Lys Ile Leu Leu Leu Gln Ala Tyr
        115                 120                 125

Arg Phe His Ala Cys Val Leu Gln Leu Pro Phe His Gln Gln Val Trp
    130                 135                 140

Lys Asn Pro Thr Phe Phe Leu Arg Val Ile Ser Asp Thr Ala Ser Leu
145                 150                 155                 160

Cys Tyr Ser Ile Leu Lys Ala Lys Asn Ala Gly Met Ser Leu Gly Ala
                165                 170                 175

Lys Gly Ala Ala Gly Pro Leu Pro Ser Glu Ala Val Gln Trp Leu Cys
            180                 185                 190

His Gln Ala Phe Leu Leu Lys Leu Thr Arg His Arg Val Thr Tyr Val
        195                 200                 205

Pro Leu Leu Gly Ser Leu Arg Thr Ala Gln Thr Gln Leu Ser Arg Lys
    210                 215                 220

Leu Pro Gly Thr Thr Leu Thr Ala Leu Glu Ala Ala Asn Pro Ala
225                 230                 235                 240

Leu Pro Ser Asp Phe Lys Thr Ile Leu Asp
                245                 250
```